US006451619B1

(12) United States Patent
Catt et al.

(10) Patent No.: US 6,451,619 B1
(45) Date of Patent: *Sep. 17, 2002

(54) MONITORING METHODS AND DEVICES FOR USE THEREIN

(75) Inventors: Michael Catt, Northampton; Carole R Cunningham, Bedford; Paul HC Mundill, Northampton; Michael E Prior, Northampton; Stewart Wilson, Northampton; Zhi G Zhang, Bedford, all of (GB)

(73) Assignee: Inverness Medical Switzerland GmbH, Zug (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/532,457

(22) Filed: Sep. 22, 1995

Related U.S. Application Data

(63) Continuation-in-part of application No. 08/266,776, filed on Jun. 29, 1994, now abandoned, and a continuation-in-part of application No. 08/338,141, filed on Nov. 9, 1994.

(30) Foreign Application Priority Data

| Sep. 23, 1994 | (GB) | ................................. 9419264 |
| Sep. 26, 1994 | (GB) | ................................. 9419382 |
| Jan. 31, 1995 | (GB) | ................................. 9501863 |

(51) Int. Cl.$^7$ ............................................. G01N 33/543
(52) U.S. Cl. ................. 436/514; 436/165; 436/169; 436/65; 435/7.92; 435/7.93; 435/7.94; 435/7.9; 435/7.1; 422/56; 422/58; 422/61
(58) Field of Search ................. 436/514, 165, 436/169, 65; 435/7.92, 7.93, 7.94, 7.9, 7.1; 422/56, 58, 61

(56) References Cited

U.S. PATENT DOCUMENTS

| 3,141,740 A | 7/1964 | Wild |
| 3,406,015 A | 10/1968 | Foster |
| 3,406,016 A | 10/1968 | Foster et al. |
| 3,434,801 A | 3/1969 | Scherr |
| 3,436,186 A | 4/1969 | McSweeney et al. |
| 3,749,089 A | 7/1973 | Derr |
| 3,875,013 A | 4/1975 | Manautou et al. |
| 3,924,609 A | 12/1975 | Friedenberg et al. |
| 3,926,037 A | 12/1975 | Kopito et al. |
| 3,968,011 A | 7/1976 | Manautou et al. |
| 3,986,494 A | 10/1976 | Preti et al. |
| 3,991,174 A | 11/1976 | Grundman |
| 4,002,056 A | 1/1977 | Kopito et al. |
| 4,010,738 A | 3/1977 | Preti et al. |
| 4,013,066 A | 3/1977 | Schuster |
| 4,031,365 A | 6/1977 | Raggiotti et al. |
| 4,036,212 A | 7/1977 | Karuhn |
| 4,059,986 A | 11/1977 | Schuster |
| 4,072,045 A | 2/1978 | Kopito |
| 4,119,089 A | 10/1978 | Preti et al. |
| 4,123,510 A | 10/1978 | Banik et al. |
| 4,148,304 A | 4/1979 | Mull |
| 4,151,831 A | 5/1979 | Lester |
| 4,151,833 A | 5/1979 | Polishuk |
| 4,208,187 A | 6/1980 | Givner |
| 4,232,215 A | 11/1980 | Hanley |
| 4,246,907 A | 1/1981 | Bullock |
| 4,261,371 A | 4/1981 | Reading, III |
| 4,312,360 A | 1/1982 | Conway et al. |
| 4,367,527 A | 1/1983 | Desjacques |
| 4,370,727 A | 1/1983 | Bellet |

(List continued on next page.)

FOREIGN PATENT DOCUMENTS

| CA | 1 048 001 | 2/1979 |
| CA | 1 183 080 | 2/1985 |
| DE | 1 214 438 | 4/1966 |
| DE | 28 03 152 | 7/1979 |
| DE | 28 47 397 | 5/1980 |
| DE | 3 037 977 | 5/1982 |
| DE | 3 221 999 | 4/1983 |
| DE | 3 247 750 | 6/1984 |
| DE | 3 314 442 | 11/1984 |
| DE | 3 325 598 | 1/1985 |
| DE | 3 342 251 | 5/1985 |
| DE | 3 343 020 | 6/1985 |
| DE | 3 528 964 | 2/1987 |
| DE | 3 609 956 | 10/1987 |
| DE | 3 802 479 | 8/1989 |
| EP | 0 097 851 | 6/1983 |
| EP | 0 132 119 | 7/1984 |
| EP | 0 011 594 | 12/1984 |

(List continued on next page.)

OTHER PUBLICATIONS

Adlercreutz et al., "Prediction of ovulation by urinary estrogen assays", J. Steroid Biochem, 1980, v. 12, pp 395–348.

Adlercreutz et al., "The measurement of urinary sterioid glucuronides as indices of the fertile period in women", J. Steroid Biochem, 1982, v. 17, pp 695,702.

Albertson et al., "Review Article: The prediction of ovulation and monitoring of the fertile period", Adv. Contracept, v. 3, pp 263–290.

(List continued on next page.)

*Primary Examiner*—Jennifer E. Graser
(74) *Attorney, Agent, or Firm*—Oppedahl & Larson LLP

(57) ABSTRACT

Methods, devices and test kits for monitoring the ovulation cycle, involve testing the body fluid, e.g. urinary, concentration of one or more analytes. Preferably estrone-3-glucuronide and luteinizing hormone are both measured, and a reference concentration for E3G is established at about day 6 of the current cycle. Preferably, disposable testing devices are used, in conjunction with a relatively permanent electronic reader/monitor. The number of "daily" tests required per month can be minimized.

11 Claims, 8 Drawing Sheets

U.S. PATENT DOCUMENTS

| | | |
|---|---|---|
| 4,377,171 A | 3/1983 | Wada |
| 4,381,121 A | 4/1983 | Hanley |
| 4,385,125 A | 5/1983 | Preti et al. |
| 4,396,020 A | 8/1983 | Wolff et al. |
| 4,408,905 A | 10/1983 | Ehrenkranz |
| 4,443,851 A | 4/1984 | Lin |
| 4,450,239 A | 5/1984 | Chatterton |
| 4,465,077 A | 8/1984 | Schneider |
| 4,466,445 A | 8/1984 | Abrams |
| 4,475,158 A | 10/1984 | Elias |
| 4,488,560 A | 12/1984 | Takamura |
| 4,498,481 A | 2/1985 | Lemke |
| 4,530,366 A | 7/1985 | Nessi et al. |
| 4,534,362 A | 8/1985 | Schumacher et al. |
| 4,557,273 A | 12/1985 | Stoller et al. |
| 4,614,715 A | 9/1986 | Tsibris et al. |
| 4,670,401 A | 6/1987 | Cutler et al. |
| 4,676,254 A | 6/1987 | Frohn |
| 4,685,471 A | 8/1987 | Regas et al. |
| 4,691,714 A | 9/1987 | Wong et al. |
| 4,737,619 A | 4/1988 | Freedom |
| 4,752,880 A | 6/1988 | Aeschlimann |
| 4,753,247 A | 6/1988 | Kirsner |
| 4,770,186 A | 9/1988 | Regas et al. |
| 4,779,627 A | 10/1988 | Kosasky |
| 4,921,808 A | 5/1990 | Schneyer et al. |
| 5,043,888 A | 8/1991 | Uriarte |
| 5,050,612 A | 9/1991 | Matsumura |
| 5,063,930 A | 11/1991 | Nucci |
| 5,091,170 A | 2/1992 | Navot |
| 5,137,028 A | 8/1992 | Nishimura |
| 5,209,238 A | 5/1993 | Sundhar |
| 5,216,599 A | 6/1993 | Uebe et al. |
| 5,248,593 A | 9/1993 | Hubner-Parajsz et al. |
| 5,467,778 A | * 11/1995 | Catt et al. .................... 128/738 |
| 5,504,013 A | * 4/1996 | Senior ........................ 436/165 |

FOREIGN PATENT DOCUMENTS

| | | |
|---|---|---|
| EP | 0 195 207 | 1/1986 |
| EP | 0 225 054 | 10/1986 |
| EP | 0 286 743 | 4/1987 |
| EP | 0 339 092 | 12/1987 |
| EP | 0 291 194 | 4/1988 |
| EP | 0 367 615 | 11/1989 |
| EP | 0 177 994 | 1/1990 |
| EP | 0 383 619 | 2/1990 |
| EP | 0 385 621 | 2/1990 |
| EP | 0 383 619 | 8/1990 |
| EP | 0 385 621 | 9/1990 |
| EP | 0 424 102 | 10/1990 |
| EP | 0 470 507 | 8/1991 |
| EP | 0 476 703 | 9/1991 |
| EP | 0 498 303 | 1/1992 |
| EP | 0 653 625 | 11/1994 |
| FR | 2 290 876 | 6/1976 |
| FR | 2 652 092 | 3/1991 |
| GB | 945670 | 1/1964 |
| GB | 1 203 619 | 8/1970 |
| GB | 2 045 480 | 10/1980 |
| GB | 2 106 646 | 4/1983 |
| GB | 2 116 318 | 9/1983 |
| GB | 2 186 977 | 8/1987 |
| WO | WO 80/02800 | 12/1980 |
| WO | WO 84/03381 | 8/1984 |
| WO | WO 87/02774 | 5/1987 |
| WO | 8808534 | * 11/1988 |
| WO | WO 90/11521 | 10/1990 |
| WO | WO 91/15594 | 10/1991 |
| WO | WO 94/02850 | 2/1994 |
| WO | 9404926 | * 3/1994 |
| WO | WO 94/04926 | 3/1994 |
| WO | WO 95/16920 | 6/1995 |

OTHER PUBLICATIONS

Baird et al., "Using the ratio of urinary oestrogena nd progesterone metabolites to estimate day of ovulation", Statistics in Medicine, 1991, 10, pp 255–266.

Barnard et al., "A nonseparation, time–resolved fluoroimmunoassay to minitor ovarian function and predict potential fertility in women", Fertility and Sterility, 1989, 52(1), pp 60–65.

Bieglmayer et al., "Evaluation of a simple and fast self–test for urine luteinizing hormone", Fertility and Sterility, 1990, 53(5), pp 842–846.

Bischof et al., "Comparison of a rapid, quantitative and automated assay for urinary luteinizing hormone (LH), with an LH detection test, for the prediction of ovulation", Human Reproduction, 1991, 6(4), pp 515–518.

Bonnar, "Biological methods of identifying the fertile period", Fertility and Sterility, 1984, Eds. Harrison et al., MTP Press, pp 77–92.

Brown et al., "Appendix 1: Correlations between the mucus symptoms and the hormone markers of fertility throughout reproductive life", The Ovulation Method, $7^{th}$ Ed., Ed. Bilings, Advocate Press, Melbourne, 1983, pp 99–125.

Brown et al., "Natural Family Planning", Am. J. Obstet. Gynecol, 1987, 157(4), Part 2, pp 1082–1089.

Brown et al., "Chemical and homogeneous immunoassay methods for the measurement of estrogens and pregnanediol and their glucuronides in urine", Non–Radiometric Assays: Technology and Application in Polypeptide and Steroid Hormone Detection, Publ. Alan R. Liss Inc., 1988, pp 119–138.

Brown et al., "New assays for identifying the fertile period", Int. J. Gynecol Obsted, Suppl. 1, 1989, pp 111–122.

Burger, "The physiologica basis of the fertile period", Fertility and Sterility, Eds. Harrison et al., MTP Press, 1984, pp. 51–58.

Burger, Estradiol: the physiological basis of the fertile period:, Int. J. Gynecol Obstet, Suppl 1, 1989, pp 5–9.

Campbell, "Methods of monitoring ovarian function and predicting ovulation: summary of a meeting", Research Frontiers in Fertility Regulation, 1985, 3(5), pp 1–16.

Cardone et al., "Objective and subjective data for fertile period diagnosis in women: comparison of methods", Clin Exp Obst Gyn, XIX, 1992, 1, pp 15–24.

Cekan et al., "The prediction and/or detection of ovulation by means of urinary steroid assays", Contraception, 1986, 33(4), pp 327–345.

Collins et al., "The concentrations of urinary oestrone–3–glucuronide, LH and pregnanediol–3a–gluronide as indices of ovarian function", Acta Endocrinologica, 1979, 90, pp 336–347.

Collins et al., "Biochemical indices of the fertile period in women", Int J Fertil, 1981, 26(3), pp 196–202.

Collins et al., "Ovulation prediction and detection by the measurement of steroid glucuronides", Proc X Int Congress on Fertility and Sterility, 1981, pp 19–33.

Collines et al., "Biochemical methods for predicting ovulation", Fertility and Sterility, 1984, pp 59–69.

Collins, "Hormonal indices of ovulation and the fertile period", Adv Contracept, 1985, 1, pp 279–294.

Collines, "Biochemical indices of potential fertility", Int J Gynecol Obstet, 1989, Supl. 1, pp 35–43.

Collins et al., "Ovarian morphology, endocrine function and intra–follicular blood flow during the peri–ovulatory period", Human Reproduction, 1991, 6(3), pp 319–324.

Collins (1991) *Am J Obstet Gynecol*, 165(6), p 1994–1996: 'The ecolution of reference methods to monitor ovulation'.

Collins (1992) *Biochem Soc Trans*, 20, p 234–237: 'Immunochemical tests of potential fertlity'.

Colombo (1989) *Int J Gynecol Obstet, Suppl 1*, p 13–18: 'Biometrical research on some parameters of the menstrual cycle'.

Corsan et al *Fertility and Sterility*, (1990) 53(4), p 591–601: 'Home urinary luteinizing hormone immunoassays: clinical applications'.

Denari et al (1981) *Obstetrics& Gynecology*, 58 (1), p 5–9: 'Determination of Ovarian Function Using First Morning Urine Steroid Assays'.

Djerassi (1990) *Science*, Jun. 1, 1990, p 1061–1062: 'Fertility Awareness: Jet–Age Rhythm Method?'.

Fabres et al (1993) *Human Reproduction*, 8, p 208–210: 'Validation of the dual analyte assay of the oestrone:pregnanediol ratio in monitoring ovarian function'.

Flynn (1989) *Int J Gynecol Obstet, Suppl 1*, p 123–127: 'Natural family planning and the new technologies'.

Fordney–Settlage (1981) *Int J Fertil*, 26, p 161–169: 'A Review of Cervical Mucus and Sperm Interactions in Humans'.

France et al (1975) *J Reprod Fert, Suppl*22, p 107–120: 'The Detection of Ovulation in Humans and its Applications in Contraception'.

Garcia et al (1981) *Fertility and Sterility*, 36(3), p 308–315: 'Prediction of the Time of Ovulation'.

Gudgeon et al (1989) *The Medical Journal of Australia*, 152, p 344, 346 and 349: 'Evaluation of the accuracy of the home ovulation detecton kit, Clearplan, at predicting ovulation'.

Hatcher et al (1994) *Contraceptive Technology*, 16th Revised Edn, Irvington Publishers, NY, p 327–340: 'Fertility Awareness'.

Ismail et al (1989) *Contraception*, 39(1), p 53–71: 'An evaluation of Bioself 110 fertility indicator'.

Judge et al (1978) *Steroids*, 31(2), p 175–187: 'Time–Course Relationships between Serum LH, Serum Progesterone and Urinary Pregnanediol Concentrations in Normal Women'.

Katz et al (1991) *Journal of Andrology*, Jan./Feb. 1991, Abstract 29: 'Human Cervical Mucus Properties and Sperm Mucus Interection during the Proliferative Phase of the Menstrual Cycle'.

Katz (1991) *Am J Obstet Gynecol*, 165(6), Part 2, p 1984–1986: 'Human cervical mucus: Research update'.

Kerin et al (1981) *British J Obstet Gynecol*, 88(2), p 81–90: 'Morphological and Functional Relations of Graafian Follicle Growth to Ovulaton in Women Using Ultrasonic, Laparoscopic and Biochemical Measurements'.

Lauzon et al (1992) *J Steroid Biochem Molec Biol*, 42(2), p 223–228: 'A Direct Dot–Enzyme Immunoassay to Detect Human Ovulation'.

Lewis et al (1993) *New Zealand Medical Journal*, Apr. 28, 1993, p 165–166: 'Recycling ovulation markers'.

Lewis et al (1994) *Steroids*, 59, p 288–291: 'Re–examining steroid hormone metabolites as ovulation markers using monoclonal antibodies'.

Landgren et al (1980) *Acta Endocrinologica*, 94, p 89–98: 'Hormonal profile of the cycle in 68 normally menstruating women'.

May (1989) *Proceedings of "Biotec '89" Conference*, Blenheim Online Publications, p 291–295: 'Clearblue One Step: adapting technology to the needs of the consumer'.

Moghissi et al (1972) *Am J Obstet Gynecol*, 114(3), p 405–418: 'A composite picture of the menstrual cycle'.

Moghissi (1980) *Fertility and Sterility*, 34(2), p 89–98: 'Prediction and Detection of Ovulation'.

Moghissi (1992) *Reproductive Endocrinology*, 21(1) p 39–55: 'Ovulation Detection'.

Munro et al (1991) *Clin Chem*, 37 (6), p 838–844: 'Relationship of Serum Estradiol and Progesterone Concentrations to the Excretion Profiles of Their Major Urinary Metabolites as Measured by Enzyme Immunoassay and Radioimmunoassay'.

Paz et al (1990) *Gynecol Obstet Invest*, 29, p 207–210: 'Determination of Urinary Luteinizing Hormone for Prediction of Ovulation'.

*Population Reports*, Series 1, No 3, Sep. 1991, p 1–33 – 1–71: 'Periodic Abstinence: How well do new approaches work?'.

Royston (1982) *Biometrics*, 38, p 397–406: 'Basal Body Temperature, Ovulation and the Risk of Conception, with Special Reference to the Lifetimes of Sperm and Egg'.

Royston (1991) *Statistics in Medicine*, 10, p 221–240: 'Identifying the Fertile Phase of the Human Menstrual Cycle'.

Schiphorst et al (1985) *Fertility and Sterility*, 44(3), p 328–334: 'An estrogen test to determine the times of potential fertility in women'.

Singh et al (1984) *Fertility and Sterility*, 41(2), p 210–217: 'Clinical validation of enzymeimmunoassay of human luteinizing hormone (hLH) in the detection of the preovulatory luteinizing (LH) surge in urine'.

Singh et al (1984) *Hormone Receptors in Growth andReproduction*, ed Saxena et al, Raven Press, NY, p 341–350: 'Clinical Validation of Enzyme Immunoassay for the Detection of the Preovulatory Luteinizing Hormone Surge in Urine'.

Stanczyk et al (1980) *Am J Obstet Gynecol*, 137(4), p 443–450: 'Direct radioimmunoassay of urinary estrogen and pregnanediol glucuronides during the menstrual cycle'.

Tsibris et al (1989) *Int J Gynecol Obstet, Suppl*1, p 73–82: 'Cervical mucus enzymes as markers of the woman's fertile period'.

Vermesh et al (1987) *Fertility and Sterility*, 47(2), p 259–264: 'Monitoring techniques to—predict and detect ovulation'.

Weerasekera et al (1983) *J Steroid Biochem*, 18(4), p 465–470: 'Multiple Immunoassay: The Simultaneous Measurement of Two Urinary Steroid Glucuronides as an Index of Ovarian Function'.

WHO Task Force (1980) *Am J Obstet Gynecol*, 138(4), p 383–390: 'Temporal relationships between ovulation and defined changes in the concentration of plasma estradiol–17beta, luteinizing hormone, follicle–stimulating hormone, and progesterone'.

WHO Task Force (1981) *Am J Gynecol Obstet*, 139(8), p 886–895: 'Temporal relationships between ovulation and defined changes in the concentration of plasma estradiol–17beta, luteinizing hormone, follicle–stimulating hormone, and progesterone. II. Histologic dating'.

WHO Task Force (1983) *Fertility and Sterility*, 39(5), p 647–655: 'Temporal relationships between indices of the fertile period'.

WHO Task Force (1983) *Fertility and Sterility*, 40 (6), p 773–778: 'A prospective multicentre trail of the ovulation method of natural family planning. III. Characteristics of the menstrual cycle and of the fertile phase'.

WHO Task Force (1985) *Int J Fertil*, 30(3), p 18–30: 'A Prospective Multicentre Study to Develop Universal Immunochemical Tests for Predicting the Fertile Period in Women'.

Wright et al (1979) *Steroids*, 34(4), p 445–457: 'Urinary excretion of estrone glucosiduronate, 17beta–estradiol–17–glucosiduronate, and estriol–16alphaglucosiduronate. Significance of proportionate differences during the menstrual cycle. I. Probit analysis'.

Yong et al. (1989) *Aust NZ J Obstet Gynecol*, 29, p 155–160: 'Simple Office Methods to Predict Ovulation: The Clinical Usefulness of a New Urine Luteinizing Hormone Kit Compared to Basal Body Temperature, Cervical Mucus and Ultrasound'.

Zinaman et al (1989) *Biology of Reproduction*, 41, p 790–797: 'The Physiology of Sperm Recovered from the Human Cervix: Acrosomal Status and Response to Inducers of the Acrosome Reaction'.

\* cited by examiner

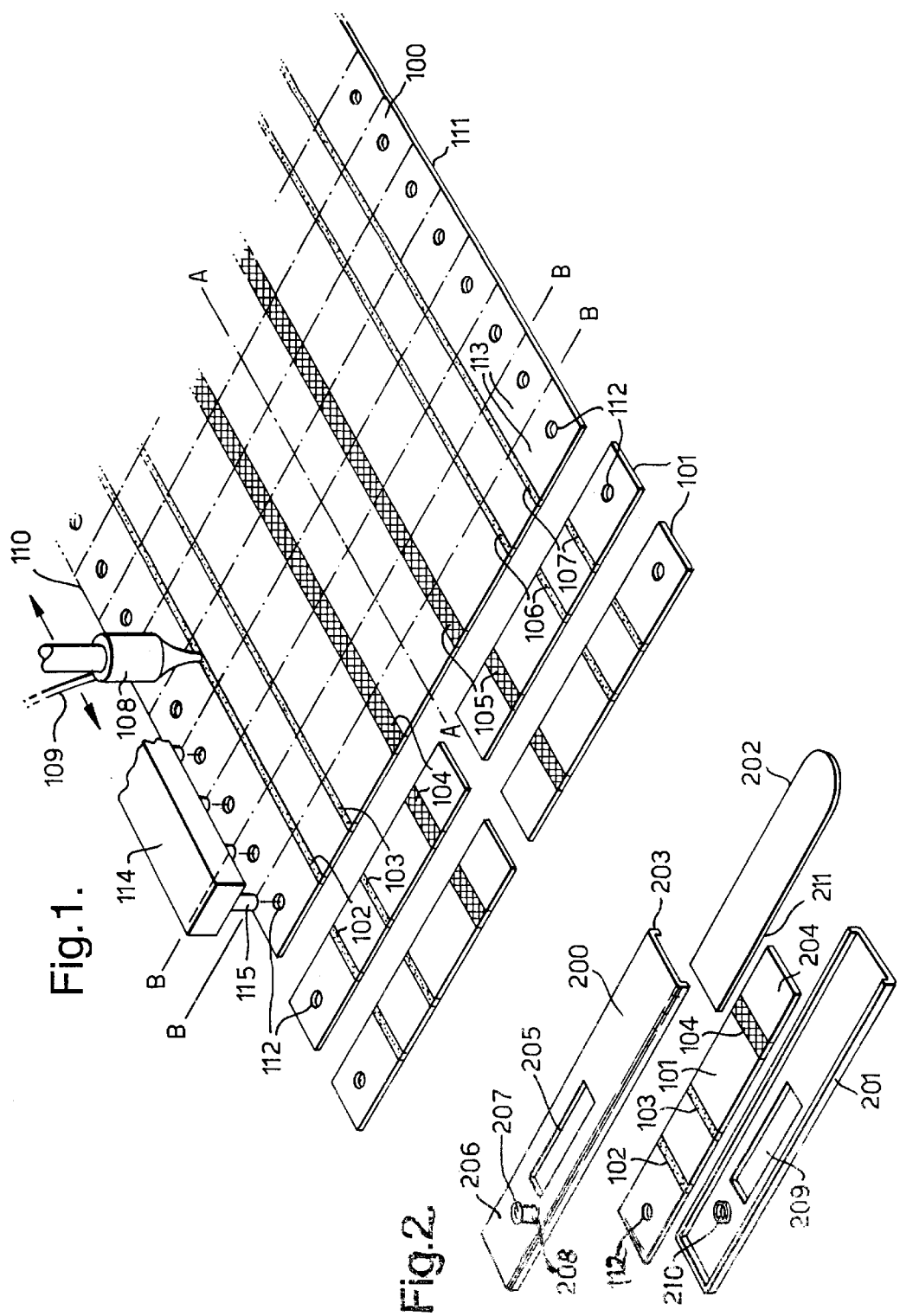

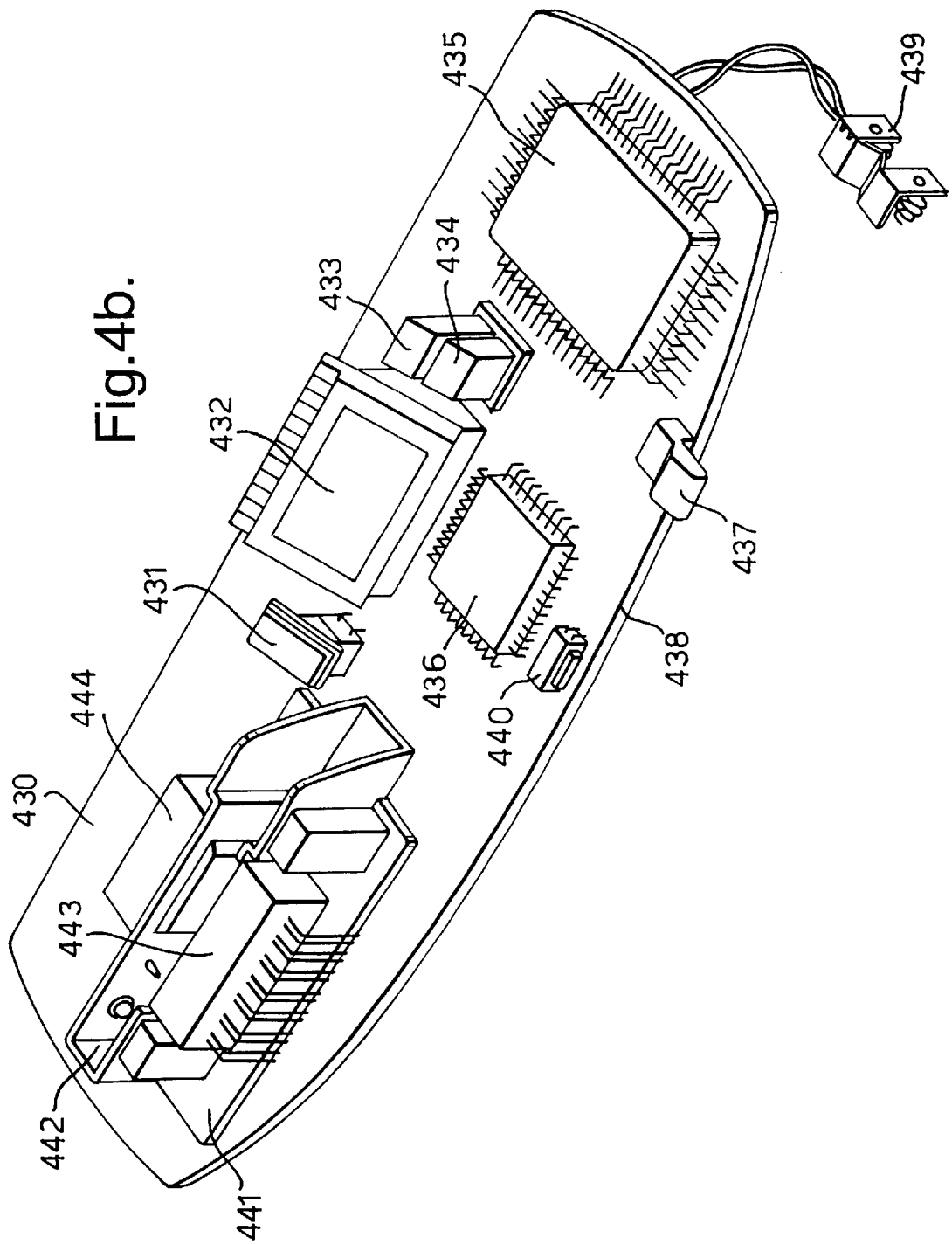

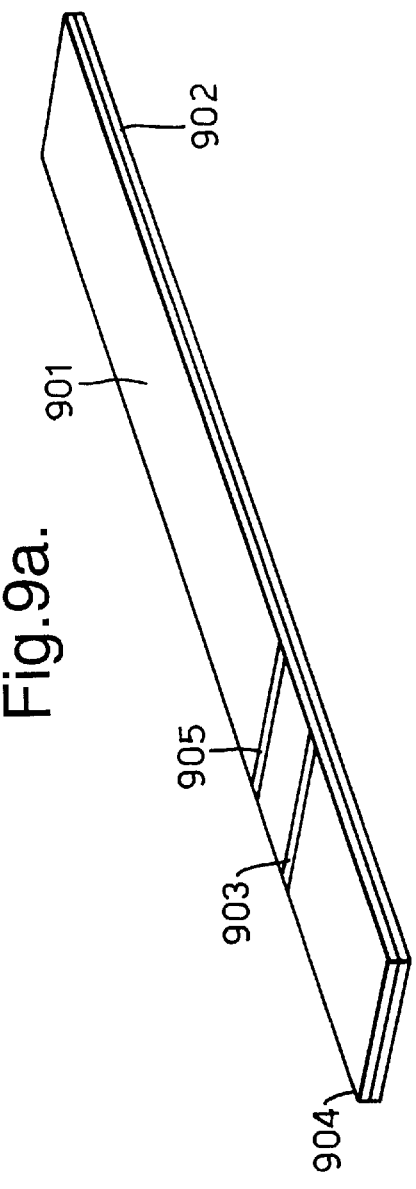
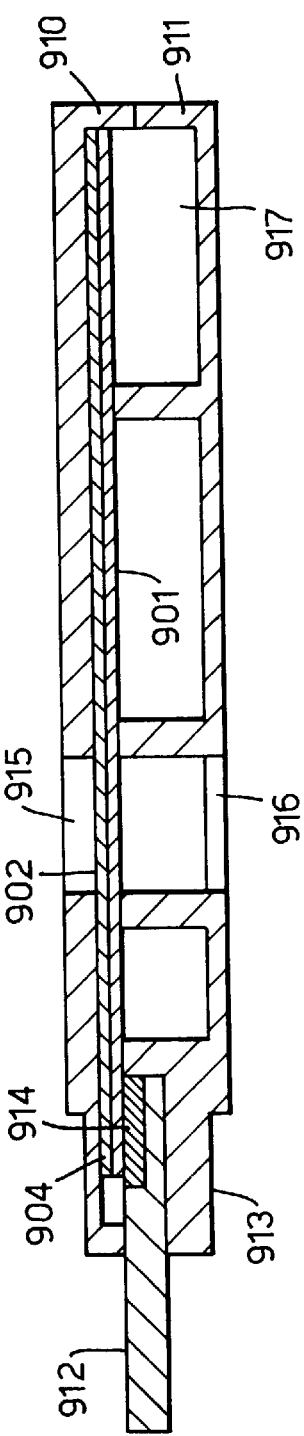

MONITORING METHODS AND DEVICES FOR USE THEREIN

This is a continuation-in-part of Ser. No. 08/266,776, filed Jun. 29, 1994, now abandoned, and Ser. No. 08/338,141, filed Nov. 9, 1994.

FIELD OF THE INVENTION

This invention relates to methods devices and test kits for use in monitoring the ovulation cycle in female mammals especially humans.

The invention is particularly, although not solely, concerned with simple practical procedures that can readily be applied by unskilled persons, e.g. in the home, to provide reliable information concerning fertility status as an aid to contraception. An important objective of the invention is to provide such information while avoiding the necessity for tests to be conducted on a frequent (eg. daily) basis throughout every ovulation cycle. The necessity for regular, e.g. daily, testing throughout the cycle has characterised many ovulation cycle monitoring systems previously proposed.

The invention may also be used by persons wishing to enhance the likelihood of conception, by providing an indication of the time during the ovulation cycle when fertilization is most likely to occur.

BACKGROUND OF THE INVENTION

To provide reliable information concerning fertility status, the user must be given adequate warning of the onset of the fertile phase in the cycle. A wide variety of techniques have proposed in the art, some relying on the monitoring of one or more parameters which alter as the event of ovulation approaches. Typical parameters which have been invoked are the concentration of a body fluid analyte, such as estradiol and metabolites thereof, for example estrone-3-glucuronide (E3G). Other parameters that have been used are basal body temperature (which can only provide predictive information of use in subsequent cycles) and various physiological changes such as the characteristics of vaginal muccus.

Many excellent academic studies have been carried out using such parameters. Such studies have established how these parameters can be correlated with the fertility status of an average member of a large population sample. An example is Collins et al (1981) *Proc. Xth International Congress on Fertility and Sterility*, Publ MTP Ltd, p 19–33. An underlying objective in many such studies is to promote conception in individuals previously regarded as being infertile.

However, when attempting to develop a practical monitoring system suitable for use by individuals, it is found that many individual subjects do not conform to the average in terms of cycle length and/or the duration and timing of the fertile phase. The extend of variation from one individual to another, and indeed, from one cycle to another in the same individual, renders average population data too unreliable for consistent practical use.

Understandably, because the severe consequence of imperfect advice concerning fertility status may be an unwanted pregnancy, the tendency has been to exercise extreme caution and to require testing of the relevant parameter or parameters throughout the cycle, and particularly right from the onset of the cycle (onset of menses). From the individual user's point of view, it would be advantageous if the necessity for such constant testing could be avoided and, instead, for the testing to be performed over a comparatively brief portion of each cycle. Not merely may this benefit the user in terms of convenience, but the cost of the method may also be reduced if the method utilises disposable testing devices and only a few such disposable testing devices are required each month.

An example of a system for detecting the onset of ovulation, using water-swellable polymer pellets to "measure" the water content of vaginal mucus, which, apparently increases at the time of ovulation, is described in U.S. Pat. No. 4,151,833 (Polishuk). It is stated that the peak variation in the size of the pellets, as a result of the absorption of water from cervical mucus, is closely related to the LH surge and the variation in basal body temperature. From the experimental data provided in U.S. Pat. No. 4,151,833 (FIG. 8), it appears that the pellet diameter is indeed very closely related to the timing of the LH surge, and in consequence the system proposed cannot in practice provide a reliable warning of the onset of ovulation earlier than that obtainable from a knowledge of the LH concentration.

In EP-A-385621 (Coley et al/Unilever) the defects of ovulation cycle monitoring systems which rely primarily on the change in BBT to estimate the time of ovulation are described, and we propose therein a system which uses regular BBT measurement in combination with a knowledge of other parameters, particularly the measurement of certain urinary hormone levels. A particular proposal is that BBT is measured daily throughout each cycle and is used to estimate the timing of fertility status changes in a forthcoming cycle. During the course of this forthcoming (predicted) cycle, urinary hormone levels are checked at certain times to confirm that the progress of the cycle, as predicted from the previous BBT knowledge, is consistent. Particular hormones selected are E3G, P3G and LH. It is suggested that the level of urinary E3G is measured on at least one day during the interval from day 5 to 7 of the predicted cycle, and again on at least one day during the interval from day 10 to day 15 of the predicted cycle. According to the example in EP 385621, it is sufficient for the hormone level to be either "high" or "low" relative to a threshold value. The emphasis throughout EP 385621 is that occasional hormone level measurements are used to supplement a monitoring system which relies on BBT measurement. There is no suggestion that hormone measurements alone could provide the basis for a reliable fertility monitoring system personalised for an individual subject.

OBJECTIVES OF THE INVENTION

An objective of the present invention is to provide a system for monitoring the fertility status of an individual subject, which provides sufficient warning of the onset of the fertile phase to enable contraceptive advice to be given and which can be personalised to the individual subject, while being based solely on body fluid analyte measurements. The inherent unreliability, or limited usefulness, of other measuring systems (such as BBT) can thereby be avoided. A further objective is to avoid the use of average data obtained from population studies, with its inherent risk that in an individual subject, the parameter under test can fluctuate considerably from the population norm.

Another objective of the invention is to provide a monitoring system which is "fail-safe", in terms of advising the user of the onset of the fertile phase, without denying the user of the benefits of a simple overall procedure and limited testing regime.

A further objective is to provide the option of basing an effective monitoring system solely, or at least primarily, on the measurement of a single body fluid analyte, such as estradiol or a metabolite thereof. Other advantages of the invention will be apparent from the following description.

Another objective of the invention is to provide a testing regime which is a good balance between the desire to minimise the testing burden on the user and the need to give the user worthwhile advice about the fertility status.

Another objective of the present invention is to provide a method and devices for determining the presence and/or concentration of two or more analytes in a single sample liquid when at least one of the analytes is a multivalent analyte which is readily determined by means of two different specific binding agents in a "sandwich-format" complex, whereas another of the analytes is a monovalent analyte, such as a hapten, which is not amenable to determination via a sandwich-reaction.

It is a further objective of the invention to provide such a dual analyte assay method/device in which a particulate direct label is used to reveal the result of both assays.

The use of particulate direct labels is already known in simpler assay systems. Sometimes the use of particulate direct labels enables the assay result to be evaluated easily by eye. This may also be the case in assays in accordance with the present invention, although it is envisaged that in general the results of the assays will more conveniently and effectively be evaluated instrumentally.

A yet further object of the invention is to provide an assay method/device in which multiple analytes in a single sample liquid can be determined accurately in a strip-format assay device which is interpreted instrumentally using electromagnetic radiation (eg. light) passed through the thickness of the assay strip. The strip material can be translucent or transparent. The extent of binding of particle labels in a detection zone in the strip can provide a quantitative assay result, because the particles can block light or other radiation and therefore reduce the transmission of the radiation through the strip.

Another objective of the invention is to produce improved combinations of assay result reading devices and associated sample testing devices which can provide accurate quantitative assay information in a simple, quick and cost-effective manner.

GENERAL DESCRIPTION OF THE INVENTION

For the purposes of illustration only, the invention will be described in relation to the measurement of urinary analytes, and especially "E3G" (estrone-3-glucuronide) and "LH" (luteinizing hormone).

In addition to estrone-3-glucuronide already mentioned, estradiol metabolites that can also be assayed for the purposes of the invention include estradiol-3-glucuronide, estradiol-17-glucuronide, estriol-3-glucuronide, estriol-16-glucuronide and (principally for non-human subjects) estrone-3-sulphate. As will be appreciated from the following description, the invention can readily be applied to data derived from the measurement of body fluid concentrations of other analytes of significance in relation to the status of the ovulation cycle. Generally, the most suitable analytes are hormones and their metabolites. Follicle stimulating hormone (FSH) is an example. Examples of alternative body fluids, which are relatively accessible, are saliva, crevicular fluid, sweat, sebum, tears and vaginal fluid. In principle internal fluids, such as blood, can be used but are generally not preferred because they can only be accessed by invasive techniques.

The skilled reader will also appreciate that the body fluid "concentration" of the chosen analyte or analytes need not be measured in absolute terms, although this can of course be done if desired. Generally, it will be sufficient to assay an analyte in a manner which yields a signal, convertible to numerical data, related to the actual concentration, so that such data can be compared with similar data obtained at a different stage in the cycle to determine whether or not a significant change in actual concentration has occurred. Accordingly, where the specification and claims below refer to the "concentration" of an analyte, this expression should be interpreted broadly.

In one aspect, the invention provides a test kit for use in monitoring the ovulation cycle of a female mammal, especially a human, comprising a plurality of disposable testing devices for sampling and testing a body fluid, such as urine, and providing readable signals indicative of the concentrations of at least two analytes in the body fluid, said analytes being of significance in relation to the fertility status of the ovulation cycle, together with an electronic reader/monitor for reading and interpreting said readable signals to provide the user with an indication of said fertility status, wherein:

a) said readable signals are read while one of said testing devices is located within a receiving means of said reader/monitor, b) said readable signals are created by concentrating a first detectable material, preferably a labelled reagent, in a first detection zone of a porous carrier, such as a test strip, within said testing device and by concentrating a second detectable material, preferably a labelled reagent, in a second detection zone of said porous carrier, while said sampled body fluid is flowing, e.g. by capillarity, through said porous carrier, said second detection zone preferably being downstream from said first detection zone relative to a receiving portion of said testing device which is contacted with said body fluid to initiate the test;

c) said first detection zone signal is indicative of the body fluid concentration of a first analyte, preferably luteinizing hormone (LH), which exhibits a significant concentration change closely associated with the time of actual ovulation; and d) said second detection zone signal is indicative of the body fluid concentration of a second analyte, preferably estradiol or a metabolite thereof such as estrone-3-glucuronide (E3G), which exhibits a significant concentration change in advance of the onset of the fertile phase of said ovulation cycle.

Preferably, said readable signals are read by optical transmission through said testing device. Ideally, to achieve this, the reader/monitor comprises:

a) a source of diffuse light having a wavelength that is strongly absorbed by said detectable materials;

b) sensing means to sense incident light from said source;

c) means for receiving and holding said testing device with each of said detection zones in a light path between said source and said sensor; and d) electronic means connected to said sensing means, said electronic means being programmed to derive from sensed incident light a measure of the extent to which detectable material has become concentrated in each of said detection zones.

Preferably said readable signals are created by concentrating particle-labelled reagents in the respective detection zones.

Preferably, the test kit contains a sufficient plurality of disposable testing devices to enable a user to conduct testing on a one-per-day basis for a maximum of 16 days in any one ovulation cycle. An important embodiment of the invention is a replacement pack, containing a plurality, preferably not more than 12, and ideally 7 to 10, of disposable testing devices to replenish a test kit preferably plus instruction to the user to use all of said testing devices during the course of one ovulation cycle.

The invention also provides a method of monitoring the human ovulation cycle, using a test kit as set forth above wherein testing s conducted at least once during the interval spanning days 1 to 7 inclusive calculated from the onset of menses, to establish a reference concentration value or signal for said second analyte in the current cycle, said testing is temporarily ceased, and then testing is conducted at least once (preferably daily) during a period of days commencing at least 5, preferably at least 6, numerical days in advance of the mean numerical day on which actual ovulation has occurred over one or more previous ovulation cycles in the same individual subject, second analyte concentration values or signals obtained during said period of days being compared with the reference concentration value or signal to determine whether a concentration change indicative of imminent ovulation is occurring or has occurred since the previous test. As a preferred fail-safe feature, the start of the fertile phase is declared if the expected significant change in second analyte concentration has not been detected prior to at least 2, preferably at least 3, days before the numerical day in the current cycle on which actual ovulation is predicted to occur, based on knowledge derived from first analyte concentration measurements obtained in one or more previous cycles.

More generally the invention provides a method of monitoring the fertility status of an individual female mammalian subject, involving testing of the body fluid concentration of an analyte, especially estradiol or a metabolite thereof, in which method said testing is conducted at least once during the interval spanning days 1 to 7 inclusive of the current cycle, to establish a reference concentration value or signal for the current cycle, and said testing is also conducted later in the current cycle, following a temporary cessation, and the concentration value or signal then obtained is compared to the reference value or signal.

An important aspect of the invention is a method of monitoring the current fertility status of an individual human female, involving testing of the body fluid concentration of estradiol or a metabolite thereof and comparing the test result with a reference value or signal to ascertain whether an elevated concentration indicative of imminent ovulation is present, wherein the reference value or signal for the current ovulation cycle is established by testing the body fluid concentration in the same individual at least once during the interval spanning days 1 to 7 inclusive of the current cycle.

In a preferred embodiment the invention provides a method of monitoring the current fertility status of an individual female mammal, involving the detection in the change of a parameter indicative of imminent entry into the fertile phase, wherein the start of the fertile phase is declared if the parameter change expected has not been detected prior to at least 2, preferably at least 3, days before the numerical day in the current cycle on which actual ovulation is predicted to occur, based on knowledge gained in previous cycles in the same individual. For the purposes of predicting the ovulation day, the "mean ovulation day" procedure as set out hereinbelow can be used. This fail-safe declaration of the fertile phase can be combined to advantage with any of the cycle monitoring techniques described hereinbelow.

More particularly, the invention provides a method of monitoring the current fertility status of an individual human female, involving testing of the body fluid concentration of estradiol or a metabolite thereof and comparing the test result with a reference value or signal to ascertain whether an elevated concentration indicative of imminent ovulation is present, wherein the reference value or signal for the current cycle is established by testing the body fluid concentration in the same individual at least once during the interval spanning days 4 to 7 inclusive, preferably on days 5 and/or 6, of the current cycle, testing is recommenced on day 9 of the current cycle and continued thereafter on at least a daily basis at least until a significantly elevated concentration is detected, and the status of the current cycle is declared to be "fertile" for the interval commencing on the day of significantly elevated concentration detection and for at least the immediately successive 12 days or until evidence of cycle termination (e.g. commencement of menses) is obtained, whichever occurs earlier. As an optional refinement of this method, if a significantly elevated concentration is not detected on or before day 15, the cycle is declared "fertile" for the interval lasting for at least 14, preferably 15, days immediately following day 15, or until evidence of cycle termination is obtained, if this occurs earlier.

Another important aspect of the invention is a human contraception method, involving:

a) testing the urinary concentration of estradiol or a metabolite thereof in the female partner at least once during the interval spanning days 4 to 7 inclusive, preferably on days 5 and/or 6, of the current cycle to establish a reference value or signal for the current cycle;

b) testing the urinary concentration again on an at least daily basis commencing on day 9 of the current cycle and continuing until day 15 (preferably day 14) of the current cycle; and c) avoiding unprotected intercourse during the interval lasting for at least 12 days immediately following the day on which a significantly elevated urinary concentration is detected or, if a significantly elevated urinary concentration is not detected by day 15 (preferably day 14), avoiding unprotected intercourse during the interval lasting for at least 14, preferably 15, days immediately following day 15 (preferably day 14), in either case the interval optionally being terminated earlier in the event of evidence of cycle termination (e.g. commencement of menses) being obtained.

In a first embodiment, the invention provides a method of monitoring the fertility status of an individual female mammalian subject, involving testing of the body fluid concentration of at least one analyte of significance in relation to the status of the ovulation cycle during the pre-ovulation phase, wherein testing for said analyte is conducted at least once during the interval spanning days 1 to 7 inclusive of the current cycle calculated from the onset of menses (day 1being the day on which menstruation is first observed), to establish a reference concentration value or signal for said analyte in the current cycle, and thereafter testing is conducted at least once (generally repeatedly, e.g. daily) prior to a day on which ovulation is likely to occur during the cycle, analyte concentration values or signals obtained during said later or repeated testing being compared with the reference concentration value or signal to determine whether a concentration change indicative of imminent ovulation is occurring or has occurred since the previous test.

In a preferred embodiment, the invention provides a method of monitoring the fertility status of an individual female subject, involving testing of the body fluid concentration of at least one analyte of significance in relation to the status of the ovulation cycle during the pre-ovulation phase, wherein testing for said analyte is conducted at least once during the interval spanning days 1 to 7 inclusive calculated from the onset of menses (day 1 being the day on which menstruation is first observed), to establish a reference concentration value or signal for said analyte in the current cycle, and then testing is conducted at least once (generally repeatedly, e.g. daily) during a period of days commencing at least 5, and more preferably at least 6, numerical days in advance of the mean numerical day on which actual ovulation has occurred over one or more previous ovulation cycles in the same individual subject, analyte concentration values or signals obtained during said period of days being compared with the reference concentration value or signal to determine whether a concentration change indicative of imminent ovulation is occurring or has occurred since the previous test. Generally, the repeated testing need not be commenced earlier than about 9 days in advance of the mean ovulation day.

Preferably, the concentration reference value is established from test(s) conducted during the interval spanning days 4 to 7 inclusive, more preferably from test(s) conducted on day 5 and/or day 6, and most preferably from a single test conducted on day 6.

A significant change in analyte concentration indicative of imminent ovulation, particularly appropriate when the analyte is estradiol or a metabolite thereof, will generally be noted when the ratio of the reference concentration [r] to the test concentration [i] meets the following criteria:

$$1.5 \le \frac{[i]}{[r]} \le 2.5$$

In particular, especially when the analyte is E3G and the reference value is established on day 6:

$$\frac{[i]}{[r]} \ge 2$$

If the chosen assay format by means of which concentration data is obtained yields a signal which is inversely proportional to actual concentration, as may be the case in a competition assay, it will be appreciated by the skilled reader than the relationship between [i] and [r] signals will be the inverse of those given above.

It is generally envisaged that there will be a gap of at least one day, and more usually several days, between establishment of the concentration reference value and the commencement of repeated testing, during which gap no testing need be conducted. Thus, in the ideal situation, the user performs a single test at an early stage of thee cycle, eg on day 6, a several days later commences a relatively brief schedule of repeated, eg daily testing, which is terminated after sufficient information has been derived to identify the fertile phase, preferably including an indication of the end of the fertile phase in that cycle. Typically this termination of testing will be on the day of LH surge, or within a few days thereafter, so that the remainder of the cycle is test-free.

Conveniently, the body fluid can be urine. A very suitable analyte is therefore estradiol or a metabolite thereof, such as estrone-3-glucuronide.

Preferably, in one embodiment of the invention, the mean ovulation day is derived from data collected during at least 3, and more preferably at least 5, consecutive previous cycles.

Ideally, the mean ovulation day used to calculate the time interval for the purposes of the current cycle is derived from data obtained during at least the immediately preceding cycle.

A particularly convenient method involves the determination of the mean ovulation day from data obtained from a "rolling" reference base consisting of a fixed number of consecutive cycles immediately preceding the current cycle. Preferably this rolling reference base consists of the immediately preceding 3 to 12 cycles, more preferably the immediately preceding 5 or 6 cycles. By having such a rolling reference base, any progressive "drift" in the occurrence of ovulation in the individual concerned can be picked up and accounted for in the allocation of the next repeated testing commencement day.

The invention includes a test kit comprising one or more testing devices for determining the concentration (in relative or absolute terms) of said at least one analyte in said body fluid, together with instruction advising the user to commence said testing during said time interval, and means enabling a user to derive said time interval and/or a precise testing commencement day from knowledge of the numerical day on which actual ovulation occurred during at least one previous ovulation cycle of the user.

Another independent aspect of the invention, which may nevertheless be combined to advantage with any method as set forth above, involves:

a) providing the user with a plurality of disposable body fluid testing devices, said plurality preferably being at least 7, but preferably not greater than 12; and b) directing the user to use all of said provided testing devices during a single ovulation cycle, in accordance with a predetermined testing schedule, irrespective of whether an indication of imminent ovulation has been obtained before all of said provided testing devices have been used.

Preferably, the user is directed to perform one test on day 6, and to use all of the remaining testing devices on a daily basis during the repeated testing period.

The invention also provides a kit for use in any of the methods as set forth above, comprising a plurality of disposable body fluid testing devices, together with means for reading and interpreting the results of tests performed using said testing devices.

The invention also encompasses a replenishment pack of disposable body fluid testing devices for use in any of the methods as set forth above, with directions to the user to use all of said contained disposable testing devices during the course of a single ovulation cycle. Preferably the pack contains not more than 12 testing devices, more preferably at least 7 but not more than 10 devices.

By requiring the user to use all of a numerically-small single batch or set of disposable testing devices per cycle, there are advantages both for the user and for the manufacturer of the devices. The user benefits because the "monthly" testing schedule is simplified—there is no need for a decision to be taken on when to stop the repeated testing, or about using up during subsequent cycles testing devices left over from earlier cycles. For the manufacturer, there is assurance that data for each cycle is derived from a single batch of testing devices, thus eliminating problems of standardisation that might otherwise arise, and reducing the complexity of any monitor required to interpret the test data. No activity by the user is required to ensure calibration of the assays. The disposable testing devices can be supplied in standard "monthly" replenishment packs, streamlining the packaging operation. Because the problem of "leftover" testing devices is eliminated, one possible cause for customer enquiries is also avoided.

An advantage of the methods of the present invention is that effective monitoring of the ovulation cycle can be achieved using data derived solely from the measurement of body fluid analyte concentration(s). It is unnecessary to combine this data with other parameters. In particular, there is no need to supplement this data with routine measurement of basal body temperature.

By adopting a concentration reference value from data in the early part of the current cycle, the methods of the invention avoid the need for calibration and ensure that the base-line reference is personal to the subject under test. This leads to a clearer indication of the significant pre-ovulation concentration change, compared to previously proposed methods based on day-to-day measurements.

The analyte chosen for providing the warning of imminent ovulation is not critical to the invention, provided that the analyte exhibits a detectable concentration change within the time interval between the commencement of testing (as determined herein) and a safe time in advance of actual ovulation in the current cycle.

The invention can be applied in any method of monitoring the status of a current ovulation cycle of an individual human female subject involving the measurement of a body fluid analyte of significance in relation to the status of ovulation cycle and which exhibits a detectable change during the pre-ovulation phase of the cycle occurring at least 2 and more preferably at least 3 days in advance of the day of actual ovulation.

The following description is provided, by way of example only, in relation to the urinary hormones E3G, luteinizing hormone (LH), and pregnanediol-3-glucuronide (P3G), although it will be readily appreciated that the principles of the method can be used in relation to other biochemical markers, for example the hormones estradiol and progesterone, found for example in the blood or in saliva. The method of the invention may be used in combination with observations of other physiological signs of the level of fertility in a female, of which she is aware, or can readily be made aware of, e.g. markers in other body fluids.

Ovulation day can be determined by any of the known chemical or physiological parameters, although a preferred method is by measuring the level of LH. Once the LH surge has been detected, it can be said that ovulation is imminent. Also, the day of the cycle on which ovulation has occurred can be noted for future reference. If the LH surge is detected, and hence the day of ovulation accurately pinpointed, it can be indicated to the user with a very high degree of certainty that the subject will no longer be fertile four days hence (3 days after ovulation). For practical purposes, a urinary LH concentration of 20 mIU/ml can be regarded as a universal threshold indicative of the LH surge under virtually all circumstances.

The expression "LH surge" is used herein to mean the dramatic rise in LH concentration that precedes the event of ovulation. In the art, reference is made also to "LH max", i.e. the peak concentration of LH. In the majority of individuals, these are for all practical purposes simultaneous, when the cycle is monitored on a day-by-day basis. However, in a few individuals, perhaps 20% of the population, the actual peak concentration of LH is not observed until the day following the main concentration rise. For the purposes of the invention, we prefer to use the observable rise as the critical parameter.

Alternatively, or in addition, the end of the fertile phase can be declared on the basis of knowledge of the estradiol (or metabolite thereof) concentration, in the current cycle. Conveniently, this may be declared on a set day following a peak concentration value. Because the peak concentration of urinary E3G, for example, appears to be a less readily detectable event than the LH surge, the E3 G "peak" may be defined by reference to a threshold value, determined for example by the relationship $$\frac{[i]}{[r]} > 2.5, \text{ preferably} \geq 3$$

the "peak" being taken to occur on the day when this relationship is first satisfied during the testing regime adopted in the current cycle. The inverse relationship will apply if the E3G signal in inversely proportional to actual concentration. In some instances this may be the same day as the significant E3G rise indicative of imminent ovulation is detected. When the E3G "peak" has been detected, the fertile phase can be assumed to end on the sixth, or more safely the seventh or eighth, day later. In this embodiment, the invention provides the option of a method of monitoring fertility in the current cycle based solely on data derived from estradiol/metabolite assays. For the purposes of a fail-safe procedure, based on knowledge of the ovulation day in previous cycles, the E3G peak can be used, as this typically occurs about 1 day in advance of actual ovulation.

Another method for predicting the end of the fertile period (though not so accurately the day of ovulation) is to measure the levels of the urinary hormone P3G. P3G has a relatively low level in urine until the start of the luteal phase, at which point its level rises fairly sharply. Therefore, once an elevated level of P3G is detected, it can be indicated to the user that the luteal phase of the cycle—ie. the terminal infertile period—has commenced. An elevated level of urinary P3G can be based on data taken during the current and/or one or more preceding cycles. An "elevated" P3G level can be recorded, for example, when either the level of P3G detected is greater than the sum of the four previous recorded levels of P3G in the same menstrual cycle, or greater than 3500 ng/ml, whichever of these two thresholds is lower and is first achieved. Once an "elevated" P3G level is recorded, the subject can be advised that she is infertile for the remainder of that cycle.

If desired, the detection of either LH or P3G can be used as a trigger to indicate that the subject is no longer fertile until the end of the cycle, with one hormone acting as a "back up" to the other. However, it is preferred that the detection of LH be used as a primary indicator of whether ovulation has or is about to occur, since the detection of LH lends itself to more accurate determination of the exact ovulation day than the use of P3G.

Methods of detecting body fluid analytes, such as urinary hormone metabolites, suitable for the purposes of this method, are well known to those skilled in the art. In a preferred embodiment, the analyte is detected by assay methods and devices as described in UK patent GB 2204398 and European patent application EP-A-383619.

Where the method of the invention relies on measurement of a urine component, this must be done on a urine sample. A variety of immunoassay techniques are available which enable urine components to be measured. A wide variety of solid phase testing devices such as dipsticks and chromatographic strips have been described in the literature, and can readily be adapted for use in determining urinary analytes. The device should at least be capable of indicating relative levels of analyte, eg. E3G, in threshold bands. Examples of simple assay technology that can readily be adapted for use in the home is described, for example, in EP-A-225054, EP-A-183442, EP-A-186799 and EP-A-291194. Disposble assay strips such as those described in EP-A-291194 which simply require to be contacted with urine and which provide an assay result in semi-qualitative form, eg. by means of a series of test zones on the strip which are progressively positive at higher urinary analyte levels, can be used. Multiple strips that respond at different analyte thresholds can be used, rather than a single strip. Alternatively, a visually readable quantitative assay can be based on progression of a visible, eg. coloured, region or "front" over a surface (eg. radial diffusion), using for example an enzyme-labelled assay.

In a more sophisticated embodiment of the invention, a recording device is provided which incorporates means for reading the result of the urine assay, e.g. by measuring the absorbance by or fluorescence from an assay strip. This may enable a more precise numerical indication to be given of the analyte level, and further enhance the accuracy of the method.

In an embodiment of the invention in which two or more analytes are measured simultaneously, such measurement can if desired be performed using a single body fluid testing device, eg. a device incorporating multiple assay strips, or a single strip capable of independently detecting the level of the different analytes.

GENERAL DESCRIPTION OF A PREFERRED ASSAY FORMAT

In one embodiment, this aspect of the invention relates particularly to strip-format assays for the determination of monovalent analytes such as haptens.

In another embodiment, the invention relates in particular to improved assays in which two or more analytes are determined simultaneously in the same sample.

When an assay is intended to detect the presence and/or amount of just one analyte in a sample liquid, it is relatively easy to configure the assay conditions to achieve this result and to eliminate the effect of other components that may be present in the sample. However, when it is desired to use a single assay device to determine more than one different analyte in the same sample liquid the task of "balancing" the conditions to ensure that the separate assay reactions proceed efficiently and effectively is much more difficult, especially in a strip-format assay.

In another embodiment, the invention provides a strip-format assay for a monovalent analyte (hapten) using a particulate direct label to reveal the assay result, in which assay the particulate label bears an antibody specific for the monovalent analyte and the detection zone of the strip contains immobilised analyte or an analogue thereof. Each label particle carries a multiplicity of identical antibody molecules. As a reagent, the antibody-bearing particles can be standardised during manufacture (ie. during application of antibodies to the particles) to ensure that within a given batch the loading of active antibody is constant. The concentration of analyte or analyte analogue in the detection zone should be in excess of the effective concentration (molar concentration) of antibody on the particles. It is not essential to have a constant antibody loading on each particle, because the number of particles can be varied. The quantity of particle-labelled antibody available in the assay should be in excess, relative to the anticipate analyte concentration in the sample. These levels can be adjusted by experimentation so that the presence of free analyte in the sample liquid leads to a significant level of binding of the free analyte to the antibodies on the particles and therefore significantly inhibits the possible binding of the particle label to the immobilised analyte/analogue in the detection zone. The principle behind the assay is that on the average particle there is a sufficient number of active antibody molecules to ensure binding of the particle in the detection zone, but that nevertheless the presence of analyte in the sample has a limiting effect on this binding. The extent to which the particles become bound in the detection zone is therefore inversely proportional to the concentration of analyte in the sample liquid. In a strip-format assay, the particle labelled antibody is placed upstream from the detection zone so that applied liquid sample encounters the particle labelled material and carries it to the detection zone. In this assay configuration it is necessary to ensure that the potential reaction between the free analyte and the particle-labelled antibody is at least substantially complete before these reagents reach the detection zone. The extent to which the particles bind to the immobilised analyte/analogue in the detection zone is therefore dependent on the residual uncomplexed antibody remaining on the particles. It is necessary to ensure that the concentration of immobilised analyte/analogue in the detection zone is high, to promote efficient capture of the particles as they pass through this zone. In order to enhance the efficiency of the previous binding of the particle-labelled antibody to free analyte in the sample liquid, it is very desirable that the antibody on the particles should have a very high affinity for the analyte. This affinity is preferably at least about $10^9$, and more preferably at least about $10^{10}$, litres/mole. The use of such high affinity antibodies ensures efficient capture of the free analyte by the particles, and moreover ensures that under assay conditions, once an analyte molecule has become bound to an antibody on the particle, it is very unlikely to be released or interchanged with an immobilised analyte-analogue molecule as the particle passes through the detection zone.

The general principles of the invention as set forth above apply also in an assay which is intended to determine two or more analytes, at least one of them being monovalent.

In one embodiment, the invention provides a method of determining the presence and/or concentration of two or more analytes in a single sample liquid, such as a urine sample, at least one of said analytes being determinable by means of a sandwich-format binding reaction involving two binding reagents specific for different epitopes on said analyte and at least one other of said analytes being a hapten (and therefore not determinable readily by means of a sandwich-format binding reaction), which method comprises the steps of:

a) providing a device comprising a strip of porous material along which said sample liquid can migrate, the strip having two or more spacially distinct detection zones (at least one per analyte to be determined) located downstream from the site of sample liquid addition to said strip, of which zones:
 i) at least one zone contains an immobilised capture agent being a specific binding agent for said first analyte or a specific binding agent which can capture a sandwich-format complex including said first analyte, and
 (ii) at least one other zone contains an immobilised capture agent which is either the hapten or an analogue b) providing two or more populations of particles capable of migrating through said strip with said sample liquid, of which populations:
 i) at least one population carries a binding agent specific for said first analyte, or specific for another specific binding agent which can participate in a sandwich-format reaction with said first analyte, and
 ii) at least one population other carries a binding agent specific for said hapten; and c) causing said populations of particles to become suspended in said sample liquid and to migrate with said sample liquid through said strip; the presence of said first analyte in said sample liquid leading to binding of particles in said at least one detection zone in an amount directly proportional to the concentration of said first analyte in said sample liquid, and the presence of said hapten in said sample liquid leading to a reduction in binding of particles of said at least one other population in said other detection zone in an amount directly proportional to the concentration of said hapten in said sample liquid, the detection zone containing the immobilised hapten or immobilised hapten analogue being preferably sited downstream from the detection zone associated with the first analyte.

An example of the first analyte is luteinizing hormone (LH). An example of the second analyte is estradiol or a metabolite thereof, such as estrone-3-glucuronide (E3G).

Preferably the particles are latex particles, which may be coloured.

Most preferably the affinity of the anti hapten specific binding agent is at least about $10^9$, preferably $10^{10}$, liters/mole.

Preferably the extent of particle binding in each of said detection zones is determined by measuring the extinction of electromagnetic radiation, such as light, when transmitted through the thickness of said strip.

The invention also provides an assay device for use in the determination of two or more analytes in a single sample liquid, at least one of said analytes being determinable by means of a sandwich-format binding reaction involving two binding reagents specific for different epitopes on said analyte and at least one other of said analytes being a hapten (and therefore not determinable readily by means of a sandwich-format binding reaction), the device comprising, preferably within a protective casing:

a) a strip of porous material along which sample liquid can migrate;
b) two or more detection zones (at least one per analyte to be determined) on said strip, located downstream from the site of sample liquid addition to said strip, of which zones:
  i) at least one zone contains an immobilised capture agent being a specific binding agent for said first analyte or a specific binding agent which can capture a sandwich-format complex including said first analyte, and
  ii) at least one other zone contains an immobilised capture agent which is either the hapten or an analogue thereof;
c) two or more populations of particles, located upstream from said detection zones, capable of migrating through said strip with said sample liquid, of which populations:
  i) at least one population carries a binding agent specific for said first analyte, or specific for another specific binding agent also present in the device and which can participate in a sandwich-format reaction with said first analyte, and
  ii) at least one other population carries a binding agent specific for said hapten;

the presence of said first analyte in said sample liquid leading to binding of particles in said at least one detection zone in an amount directly proportional to the concentration of said first analyte in said sample liquid, and the presence of said hapten in said sample liquid leading to a reduction in binding of particles of said at least one other population in said other detection zone in an amount directly proportional to the concentration of said hapten in said sample liquid, the detection zone containing the immobilised hapten or immobilised hapten analogue being preferably sited downstream from the detection zone associated with the first analyte.

Preferably the strip material is at least translucent through its thickness. An ideal strip material is nitrocellulose.

Because the assay for the hapten is not a competition reaction in which there is the possibility of free interchange between analyte in the sample and analyte provided as a reagent in the assay (in this case the analyte/analogue immobilised on the strip) it is essential that during the course of the assay sufficient opportunity is provided for the analyte in the sample to become bound to the antibody bearing particles before these particles encounter the relevant detection zone on the strip. To ensure this it is desirable that there is a comparatively long contact time between the particulate reagent and the sample. Accordingly within the limits of acceptable physical geometry of the assay device the detection zone containing the immobilised analyte/analogue should be as far downstream from the source of the particle labelled reagent as possible. In particular, where the assay device is intended to determine two or more analytes in the same sample liquid and at least one of the other analytes is determined by means of a sandwich-format reaction, the detection zone for the hapten should ideally be downstream from the detection zone or zones involved in the sandwich-format assays.

A particular embodiment of the invention is therefore a dual analyte strip format assay for determining LH and E3G in an applied urine sample in which the two assay results are detected in specially distinct detection zones on the strip and the E3G zone is downstream from the LH detection zone relative to the site of sample liquid application.

Assay devices comprising a strip of porous material along which liquid such as an applied sample can migrate by diffusion or capillarity to bring one or more assay reagents to a small detection zone in the strip, are now widely used for the qualitative and semi-quantitative analysis of analytes which can be detected by means of solid-phase sandwich assays. When direct labels, such as gold sols and coloured latex particles are employed, such assays can reveal the result in a form easily readable by the human eye. The result is effected by concentrating the detectable material in the comparatively small region of the porous carrier material.

In one embodiment, the invention provides a quantitative strip-formay assay in which the assay result is revealed by binding in a detection zone a labelled reagent possessing multiple active binding sites specific for the analyte under test. The label is a detectable micro-particle, such as a (coloured) latex particle, metallic (e.g. gold) sold, dye sol, or non-metallic elemental (e.g. carbon, selenium) particle, of a size sufficiently small to permit migration through the porous strip material but sufficiently large to permit the formation of a detectable end-result when the labelled material is concentrated in the detection zone. Particulate labels of the types already used in strip-format sandwich assays are ideal.

In a typical assay according to the invention, the multiple active specific binding sites in the labelled reagent are provided by having a multiplicity of identical antibodies, preferably monospecific (eg monoclonal) antibodies, attached to each label particle.

Contrary to expectation, we have found that especially in a hapten assay the use of particulate labels possessing multiple identical active analyte-specific binding sites leads to a valuable increase in sensitivity. We believe that the excess binding sites on the label particle allows effective binding of the particle in the hapten-bearing detection zone. However, perhaps because of the geometry of the system, which may be visualised as a planar detection zone surface and a more-or-less spherical label particle, the prior binding of merely a relatively small amount of hapten analyte from a sample to the curved surface of the label particle causes a degree of inhibition of binding of the label particle in the detection zone sufficient to influence the binding and cause a detectable effect.

We believe that it is highly desirable that once an analyte molecule has become specifically bound to the label particle, it should remain so bound throughout the remainder of the assay protocol leading to the formation of the detectable assay result in the detection zone. One way of achieving this is by using a specific binding agent in the labelled reagent which has a very high affinity for the analyte. It is now conventional to use monoclonal antibodies having analyte-affinities of $10^8$. We have found it advantageous to use, in the context of a strip-format hapten assay, labelled specific binding agents having analyte-affinities of at least about $10^9$ and more preferably of at least about $10^{10}$, liters/moles. A good method for measuring affinity in solution is described in Friguet et al, *J. Immunol Methods,* Vol 77 (1985) pages 305–319. Monoclonal antibodies having such high affinities can be raised in the conventional manner and identified by normal selection procedures. Although it is desirable to use antibodies which exhibit high affinity in solution, this is not the only way of achieving this aspect of the invention. It is occasionally observed that an antibody that exhibits comparatively low affinity in solution can be transformed in its effective properties when immobilised on a solid phase.

An important embodiment of the invention is a quantitative strip-format assay for human body fluid analytes, especially haptens. A particular example is such an assay for estradiol or a metabolite thereof, such as estrons-3-glucuronide (E3G). An especially important embodiment of the invention is a strip-formay assay for urinary E3G which is capable of quantitatively determining the E3G over a concentration range of 5–60 ng/ml urine. Such an assay is particularly well suited for use in a procedure intended to provide a user with an awareness of the fertility status of an ovulation cycle, the body fluid concentration of estradiol or a metabolite thereof being recognised as a useful indicator of such status.

If desired, an assay device according to the invention, as set forth above, can additionally include the ability to determine other analytes in the same sample, if appropriate by employing conventional sandwich assay technology. For example, one embodiment of the invention is a strip-format assay device which can provide a quantitative determination of urinary E3G, as set forth above, and simultaneously a quantitative determination of urinary luteinizing hormone (LH) by means of a sandwich assay procedure, the E3G and LH results being revealed in two separate detection zones. Conveniently, in such a combined assay, the label can be the same for each assay, although the skilled reader will of course appreciate that two populations of label particles would normally be required, one carrying multiple binding sites for the E3G and the other carrying a specific binding material for the LH. The E3G detection zone will contain immobilised E3G or an analogue thereof, and the LH detection zone will contain immobilised specific binding material, such as an anti-LH antibody.

GENERAL DESCRIPTION OF A PREFERRED ASSAY RESULT READING SYSTEM

This aspect of the present invention relates to devices for reading the results of assays, and to assay devices for use in conjunction with reading devices.

Home-use assay devices such as pregnancy tests are now well established. In the case of a pregnancy test, which merely needs to provide the user with a "yes/no" result, the technology now available enables the assay result to be read easily by eye without the need for any ancillary equipment.

Home-use assays are intended primarily to detect physiological changes in the human body, with the objective of promoting the health, general well-being or lifestyle of the individual. The consumer is becoming increasingly health conscious, and the ability of the consumer to monitor his or her bodily functions is being encouraged. In some instances this can facilitate the interaction between the individual consumer and the medical profession (GP).

There are many assays indicative of physiological changes in the human body which currently can only be performed using sophisticated laboratory techniques. In order to provide useful information concerning the individual under test, such assays generally need to yield a result in precise numerical terms, eg. the concentration of a specific analyte in a body fluid.

Accordingly there is a need for an assay system, especially applicable to the testing of body fluid samples in the home, which combines convenience of sample testing together with simple and cost-effective numerical determination of the assay result.

Many assay devices are described in the technical literature with suggestions that the assay result can be read using optical equipment. The use of fluorescence emission, or light reflectance, is often suggested. Such techniques are mostly appropriate for use in sophisticated laboratories. In EP-A2-212599, which describes multizone analytical elements having a detectable signal concentrating zone, the suggestion is made that a detectable signal indicative of an assay result in the zone can be measured by electromagnetic radiation, such as light, transmitted through the zone. EP-A2-212599 indicates that the element can be made from porous fibrous materials, such as paper and nitrocellulose. However, no practical details are provided to indicate how an accurate measurement might be made using transmitted light.

We have found that quantitative information can be derived by transmission reading of an assay strip or the like if the incident electromagnetic radiation is uniform across a region of the test strip which encompasses and extends beyond the test zone.

In one embodiment, the invention provides a method of "reading" the result of an assay effected by concentrating a detectable material in a comparatively small zone of a carrier in the form of a strip, sheet or layer through the thickness of which electromagnetic radiation, such as light, is transmissible, wherein at least a portion of one face of said carrier is exposed to incident electromagnetic radiation which is substantially uniform across the entire portion, said portion including said zone, and electromagnetic radiation emerging from the opposite face of said carrier is measured to determine said assay result.

Preferably, the incident electromagnetic radiation is of substantially uniform intensity.

This uniformity can be achieved, for example, by providing a columated source of electromagnetic radiation, using conventional focusing means such as lenses and light guides to provide parallel incident electromagnetic radiation which falls essentially normally across the entire exposed portion of the carrier.

However, in a more preferred embodiment of the invention, the incident electromagnetic radiation is diffuse and bathes the exposed portion of the carrier uniformly in a randomly scattered manner.

In another embodiment, the invention provides an assay device comprising a porous liquid-permeable carrier strip or sheet through the thickness of which electromagnetic radiation is transmissible diffusely, said carrier being within a casing, said carrier including at least one detection zone in which an assay result is revealed by specific binding of a detectable material directly or indirectly to a binding agent immobilised in said detection zone, detection of said material being effected as a response to said electromagnetic radiation, and said casing having electromagnetic radiation transmitting regions enabling electromagnetic energy from an external source to be passed through said device, said detection zone lying in the electromagnetic radiation path between said electromagnetic radiation transmitting regions.

Preferably, the porous carrier strip or sheet comprises paper, nitrocellulose or the like, preferably of a thickness not exceeding 1 mm.

In yet another embodiment, the invention provides an assay device and assay result reader combination, wherein:

a) said device comprises a porous liquid-permeable carrier strip or sheet through the thickness of which electromagnetic radiation is transmissible diffusely, said carrier preferably being within a casing or cover, said carrier including at least one detection zone in which an assay result is revealed by specific binding of a detectable material directly or indirectly to a binding agent immobilised in said detection zone;

b) said casing or cover, if present, has electromagnetic radiation transmitting regions enabling electromagnetic radiation from an external source to be passed through said device, said detection zone lying in a path between said transmitting regions;

c) said assay result reader has receiving means for receiving at least a portion of said device, said portion including said detection zone to present said detection zone to reading means, said reading means incorporating a source of uniform electromagnetic radiation and one or more sensors located such that upon insertion of said device into said receiving means, electromagnetic radiation can be passed through said device and the intensity of electromagnetic radiation emerging from said device can be detected by said sensor(s).

Preferably, said receiving means incorporates interlocking means engagable with corresponding interlocking means on said device to ensure that upon receipt of said device by said reader said detection zone(s) is located and maintained in a predetermined spacial relationship relative to said reading means.

Preferably, said receiving means includes actuating means triggered by said receipt of said device, said actuating means causing said reading of said detection zone(s) to be initiated.

If the assay device is provided with a casing, it is advantageous if said device casing includes internal registration means which engages with corresponding registration means associated with said carrier such that said detection zone within said device casing is located in a predetermined spacial relationship relative to said registration means on said device casing. Preferably, said internal registration means comprises a pin or the like, engagable with a hole, indentation of the like in said carrier, said detection zone being at a predetermined location on said carrier relative to said hole or indentation.

During manufacture of said assay device, said corresponding registration means may be used to facilitate or control accurate formation, e.g. by means of reagent printing techniques, of said detection zone on said carrier. In addition, or alternatively, accurate placement of said carrier within said device casing can be facilitated or controlled by said registration.

In a further embodiment, the invention provides an assay result reader, for use in conjunction with an assay device comprising a porous liquid-permeable carrier strip or sheet through the thickness of which electromagnetic radiation is transmissible, said carrier including a detection zone in which an assay result is revealed by specific binding of a detectable material directly or indirectly to a binding agent immobilised in said detection zone, detection of said material being effected as a response to said electromagnetic radiation, said assay result reader comprising:

a) receiving means for receiving at least a portion of said assay device, said portion including said detection zone;

b) reading means associated with said receiving means, said reading means comprising:
i) at least one source of uniform diffuse (preferably electromagnetic radiation; and
ii) one or more sensors capable of detecting the intensity of said electromagnetic radiation;

said source and said sensor(s) being positioned such that when said portion of said assay device is received within said receiving means, said detection zone is disposed in a path between said source and said sensor(s).

The assay device/reader combination can be supplied to the consumer as a single test kit. In general however, whereas the reader will be a relatively permanent unit which the consumer can use time and again (and which may be provided with an electronic memory/data-processing facility which enables the results of many sequential assays to be evaluated) the testing devices will be intended for use only once and thereafter will be discarded. Accordingly, the test devices may be supplied to the consumer separately from the reader, e.g. in multi-packs.

By ensuring precise interlocking between the testing device and the reader, and also ensuring precise registration of the location of the detection zone within the testing device itself, the testing zone will be presented to the reader in a constant pre-determined position every time a testing device is inserted into the reader. The construction of the optical system within the reader (light source and sensors) can therefore be kept as simple as possible, because it is not essential for the sensors to include any scanning facility, for example, which would otherwise be required if the exact location of the detection zone was not known. By avoiding the need for a sophisticated optical reading system, the cost of the reader/monitor may be reduced. Simplification of the optical reading system may also enable the reader/monitor to be of small size which will assist convenient and unobtrusive use in the home. Of course, a scanning facility can be included in the reader if desired.

An additional benefit of providing an internal registration system which ensures precise location of the detection zone within the test device, is that automated manufacture and quality control of the testing devices can be facilitated. Because it is envisaged, for example, in the case of an ovulation cycle monitor, that the consumer will need to use several testing devices each month, the testing devices may need to be manufactured in large numbers at low cost. Internal registration can facilitate automated manufacture and high throughput.

In principle, any electromagnetic radiation can be used to effect the transmission measurement in the invention. The electromagnetic radiation should preferably be capable of being rendered diffuse. Preferably the electromagnetic radiation is light in the visible or near-visible range. This includes infra-red light and ultra-violet light. It is generally envisaged that the detectable material used as a label in the assay is one which will interact with light in the visible or near visible range, eg. by adsorption. The wavelength of the electromagnetic radiation chosen is preferably at or near a wavelength which is strongly influenced, eg. absorbed, by the label. For example, if the label is a substance which is strongly coloured, ie. visible to the naked human eye when the material is concentrated, the ideal electromagnetic radiation is light of a complementary wavelength. Particulate direct labels, for example, metallic (eg. gold) sols, non-metallic elemental (e.g. Selenium, carbon) sols, dye sols and coloured latex (polystyrene) particles are ideal examples. For instance, in the case of blue-dyed latex particles, the ideal electromagnetic radiation is visible red light which will be strongly absorbed by the blue particles.

In a preferred embodiment of the invention, the transmitted electromagnetic radiation reaching the sensor(s) should be diffuse. The diffuseness may arise as a consequence of transmission of the electromagnetic radiation through the carrier strip or sheet, but more preferably is contributed by the source of the electromagnetic radiation emitting the energy in a highly diffuse form. In a preferred embodiment of the invention the source produces highly diffuse radiation and the carrier strip or sheet through which this radiation subsequently is transmitted is in comparative terms a much weaker diffuser.

A primary advantage of the use of diffuse light or other radiation in the context of the invention is that the reading of the assay result is much less likely to be adversely influenced by blemishes or contaminating material on the assay device. For example, dirt or scratches on the assay device in the region through which the radiation must be transmitted could strongly interfere with the accuracy of the determined result if focused rather than diffuse light is used. By the use of a diffuse light source in accordance with the invention, it is possible to provide an assay result reader which can accurately interpret the result of an assay conducted even in an essentially transparent assay device without the assay result being adversely affected by minor contamination or damage (eg. superficial scratches) to the assay device.

In a preferred embodiment of the invention, the electromagnetic radiation from the source is pulsed. By synchronising the detectors (sensors) so that they function only in phase with the pulsed radiation source, it is possible to eliminate any background interference that might be caused by external radiation, e.g. ambient light. It is envisaged that the assays will mostly be conducted under circumstances of natural daylight or, even more often, artificial light. Artificial light is usually of a pulsed nature (typically 50–100 Hz) caused by the alternating nature of electricity supplies. By adopting a pulsed radiation source for the illumination of the assay device within the reader, the intrusion of natural daylight can be ignored. By selecting the pulse frequency such that it is sufficiently different from the prevailing artificial light, any interference due to artificial light can also be avoided. Preferably the pulse frequency of the energy should be at least about 1 kHz. An ideal pulse frequency is about 16 kHz. The electronics necessary to achieve synchronous pulsed sensing are familiar to those skilled in the art.

The use of pulsed light is very advantageous because it renders it unnecessary for the monitor to be "light tight". Not merely does this simplify the construction of the monitor but the reading of the assay result can be performed while the monitor is "open", thus simplifying the operation for the user.

The source of light or other electromagnetic radiation can comprise entirely conventional components. Ideal examples are commercially available LED's, preferably chosen to give a suitable wavelength of light that is strongly absorbed by the detectable material concentrated in the test zone(s). Light from the LED's should be passed through a strong diffuser before reaching the assay device. If desired, an array of LED's which are energised in turn can be used.

Suitable diffusers can be made, for example, from plastics materials, and are available commercially. If necessary, the light-scattering properties of the diffusing material can be enhanced by including particulate materials such as Titanium dioxide and Barium sulphate. An ideal diffusing material comprises polyester or polycarbonate, containing Titanium dioxide. A good inclusion level for the particulate material is at least about 1% by weight, preferably about 2%. By the use of a diffuser, all relevant regions of an assay strip may be measured simultaneously, and differences in light output from the source are eliminated.

The sensor(s) to detect emergent light can be conventional components such as photodiodes, e.g. silicon photodiodes.

Preferably, a second diffuser, which can be made from the same material as the primary diffuser, is located in front of the sensor(s). This ensures that the view seen by the sensor is not affected by the presence or absence of a test strip in the reading head. In consequence, the monitor can be calibrated in the absence of a test strip, and then measure an assay result in the presence of an assay strip.

By employing a uniform light source in accordance with the invention, it is possible to provide a reading system for test strips and the like which is relatively tolerant to variation in the placement of the test zone(s) from one strip to another, in the absence of a scanning sensor. Further benefits are obtained if test zone placement is controlled, as described herein.

For the purposes of enhancing the likelihood of conception, assay devices have already been marketed which enable the user to monitor the urinary concentration of luteinizing hormone (LH) which peaks sharply approximately one day in advance of ovulation. Daily testing of urinary LH concentration is conducted, for example using "dipstick" technology with the assay result being provided by a coloured end point, the intensity of the colour being proportional to LH concentration. By providing the consumer with a colour chart which enables the daily result to be compared against a standard, the "LH surge" can be detected simply by eye. Unfortunately, the monitoring of LH concentration is a very rare example of an assay relying on semi-quantitative data which is amenable to such simple technology, being possible only because in relative concentration terms the LH surge is such a dramatic event. For most other potentially useful assays the analyte concentration changes in body fluids are much more subtle and only detectable accurately by instrumental means.

A need therefore exists to extend the currently available qualitative home-use testing technology into the area of precise quantitative testing. A convenient example, which is a logical extension of the present consumer interest in home-use pregnancy testing and ovulation prediction testing, is the extension into accurate monitoring of the ovulation cycle, not merely to enhance the likelihood of conception but indeed to provide reliable information for the purposes of contraception. Proposals have been made to analyse body fluids with this objective in mind. A common theme is to monitor periodic fluctuations in various hormone metabolite levels in urine.

The invention can be used in the determination of any body fluid analyte, especially in the monitoring of the human ovulation cycle by the determination of one or more hormones or metabolites thereof in body fluid, such as urine, for example either LH and/or estrone-3-glucuronide (E3G).

Within the preferred context of the present invention it is envisaged that a home-use sample liquid testing device will include a porous carrier material, such as a strip, through which applied sample liquid such as urine can permeate and wherein the assay result occurs by means of specific binding of a detectable material in a precisely-defined region (detection zone) of the carrier, such as a narrow line or small dot, containing an immobilized specific binding reagent. The invention is therefore concerned with ways in which localisation of a detectable material in such a detection zone can be determined accurately in a simple and cost-effective manner. Home-use devices for the analysis of urine, for example in pregnancy tests and ovulation prediction tests, are now widely available commercially. Many such devices are based on the principles of immunochromatography, and typically comprise a hollow casing constructed of plastics material containing a porous assay strip carrying pre-dosed reagents. The reagents within the device may include one or more reagents labelled with a direct label, such as a dye sol, a metallic (e.g. gold) sol, or a coloured latex (e.g. polystyrene) microparticle, which are visible to the eye when concentrated in a comparatively small test area of the strip. The user merely needs to apply a urine sample to one part of the casing to initiate the assay. The assay result becomes visible by eye within a few minutes without further action by the user. Examples of such devices aare described in EP-A-291194 and EP-A-383619. Sample collection is conveniently achieved by means of a bibulous member which forms part of the device and which can readily take up sample liquid, e.g. from a urine stream. Optionally the bibulous member can protrude from the casing of the device to facilitate sample application.

A further embodiment of the invention is an electronic device for monitoring the fertility status of the human ovulation cycle and providing a user of said device with an indication of said fertility status, comprising:

a) reading means for reading a dual-analyte assay device as described herein;

b) information processing means for determining from said reading of said assay device, body fluid sample concentration values for said at least two analytes;

c) information processing means and memory means for deriving from said determined concentration values and from previously determined concentration values an indication of the current fertility status of a human subject under test; and d) display means for communicating said current fertility status to said user of said electronic device. Preferably, the device additionally comprises receiving means for receiving said assay device, said reading means being located within said receiving means. Reading is best achieved by optical transmission through said assay device while received by said receiving means. Preferably the display means comprises one or more light sources which provides a coloured signal to said user, a variation in said fertility status being indicated by a colour change.

Other embodiments of the invention, which will be apparent from the following detailed description, include assay devices for use as part of the reader/assay device combination, methods of manufacturing such assay devices, and methods of use of such assay devices and readers.

BRIEF DESCRIPTION OF THE DRAWINGS

By way of example only, assay devices and readers in accordance with the invention will now be described with reference to the accompanying drawings, of which:

FIG. 1 shows a general view of a sheet of porous material, e.g. paper, during the course of reagent deposition on the sheet and sub-division of the sheet into assay strips.

FIG. 2 shows an "exploded" view of an assay device of the invention incorporating an assay strip made as shown in FIG. 1.

FIGS. 4a, 4b and 4c show in partially "exploded" form the main features of a complete monitor in accordance with the invention, namely:

FIG. 4a: the lid and upper half of the casing;

FIG. 4b: an electronic circuit board incorporating a reading head;

FIG. 4c: the lower half of the casing and associated battery container.

FIG. 9a shows a dual-analyte test strip.

FIG. 9b shows in longitudinal cross-section an assay device including the test strip of FIG. 9a.

FIGS. 9a and 9b are described under Example 5 below.

DETAILED DESCRIPTION OF AN ASSAY DEVICE/MONITOR COMBINATION

Figure 3:
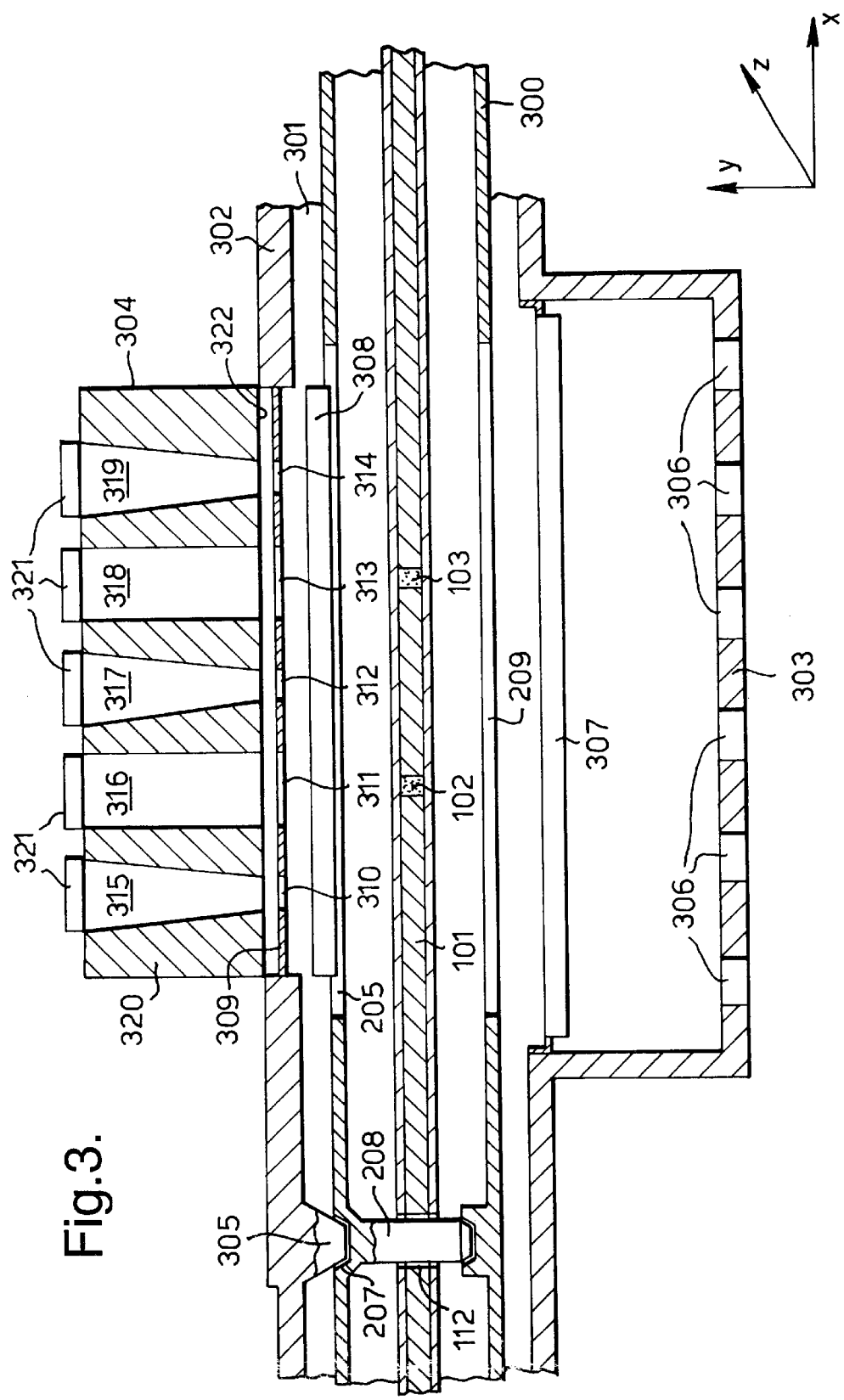
FIG. 3 shows in diagrammatic cross-section an assay device of FIG. 2 located within the reading head of a monitor in accordance with the invention, working by light transmission through the assay strip. The y axis is distorted to show the arrangement of components.

Referring to FIG. 1, the sheet 100 of porous material, e.g. nitrocellulose, is intended to be divided into a plurality of identical assay strips 101 by cutting along central axis A—A and the lateral axes B—B.

Parallel lines (102–107) of assay reagents are placed on sheet 100 prior to sub-division. For the purposes of example only, the reagents are assumed to be a first immobilised antibody in lines 102 and 107, and a second different immobilised antibody in lines 103 and 106. Reagent deposition can be by means of a "pen" 108 or the like operated on a computer-controlled "x-y" plotting mechanism (not shown) and fed with appropriate buffered reagent solution via a metered flexible tube 109. If the material of sheet 100 is nitrocellulose, reagents such as antibodies and antigens can be immobilised by simple direct application onto the nitrocellulose, followed by blocking of the sheet material, for example with albumen or polyvinyl alcohol. Following reagent deposition and blocking, two lines 104 and 105 of mobile labelled reagent, such as antigen (e.g. E3G) or another antibody (e.g. anti-LH) labelled for example with a particulate direct label such as coloured latex, can be deposited. This deposition can be for example by means of another pen (not shown). Alternatively, the labelled reagent(s) can be held in a separate porous pad or the like, rather than being applied directly to the test strip material.

In order to achieve precise location of the reagent-containing lines, each longitudinal periphery 110, 111 of sheet 100 is pierced with a plurality of identical small holes 112 each one being situated within the width of a designated strip 113. Holes 112 are made in sheet 100 prior to the deposition of any reagents. The untreated sheet is located on a frame (not shown) or similar operating surface by means of a bar 114 pressed downwardly onto each lateral periphery of the sheet. Only one of these bars is (partially) shown. Each bar has a plurality of downwardly projecting pins 115, each of which locates precisely into one of the holes 112. The tracking of the reagent-depositing pen 108 is registered precisely with the position of the bars holding the sheet, and accordingly the reagent deposition is made in a predetermined precise line relative to the perforations in the sheet.

Following all necessary reagent depositions and other treatments of the sheet, the sheet is subdivided by cutting means (not shown) into individual identical strips 101. Each individual strip therefore contains one locating hole 112 with two reagent-containing lines or reaction zones (e.g. 102 and 103) located relative to hole 112 in precise predetermined positions extending across the width of each strip. At a location remote from hole 112 is a region (e.g. 104) of the strip bearing the mobile labelled reagent. The exact position of the labelled reagent relative to the hole is not necessarily as critical as the location of the reaction zones.

Referring to FIG. 2, an assay device of the invention comprises a plastics casing having upper and lower halves 200 and 201 adapted to contain the assay strip 101 and also a bibulous sample receiving member 202 which can extend out of one end 203 of the assembled casing. In the assembled device the bibulous receiving member 202 overlaps the end 204 of the assay strip adjacent to the deposited labelled reagent. The upper half 200 of the casing includes a window or aperture 205 through which both detection zones 102 and 103 can be observed from outside the casing. Upper half of the casing contains on its external surface 206 a circular depression 207 on the central longitudinal access of the casing a short distance beyond the observation window relative to the end 203 of the casing accommodating the sample receiving member. On the inside of the upper half of the casing is a downwardly extending pin or peg 208 located directly below depression 207. The diameter of the downwardly extending pin or peg 208 matches that of the hole 112 in the assay strip 101, so that the strip can be positively located within the assembled device on the peg.

Lower half 201 of the casing also includes a light-transmitting window or aperture 209 which, in the assembled device, lies directly opposite to the result window 205 in the upper half of the casing. Lower half of the casing also contains a depression 210 which can accommodate the bottom end of the pin or peg 208 when the two halves of the casing are placed together to make an enclosure.

In the assembled device, the act of enclosing the strip and bibulous member between the upper and lower halves of the casing causes the overlapping portions 204 and 211 of the strip and bibulous member to be crimped together to provide a good moisture-conductive junction.

It is generally envisaged that the material of the casing will be opaque, e.g. white or coloured plastics material, but the casing can be translucent or indeed transparent if desired.

Referring to FIG. 3, the assay device 300 is seen located within a slot 301 in a monitor 302. This region of the assay device includes the two opposing windows 205 and 209.

The casing of the monitor is slotted to receive the portion of the assay device incorporating the result windows. On opposing sides of the slot is a light source 303 and a reading head 304.

The slot incorporated a button or projection 305 which can fit into the depression 207 on the external face of the casing of the assay device. Precise positive location of the casing within the slot is therefore achieved. Because the depression is in a fixed position relative to the internal pin or peg 208 within the assay device, and hence the registration hole 112 in the assay strip 101, the two detection zones 102 and 103 on the strip are located in a precise position relative to the reading head. The hole in the assay strip therefore acts as a positive reference throughout the manufacture of the assay device and ensures that after the device has been used and presented to the monitor the detection zones on the strip will be in the same position relative to the reading head each time. Accordingly there is no need for the reading head to incorporate a scanning facility to locate the detection zones in each presented device.

The light source or illuminator 303 incorporates a plurality of LEDs 306 to generate light, and this shines onto the assay strip via a diffuser 307 and the observation window 209 in the lower half of the assay device casing. The light passes through the thin nitrocellulose strip 101 and exits the assay device through the result window 205 in the upper half of the casing. Immediately outside window 205 is a second diffuser 308. After passing through the second diffuser 308, the light encounters a plate 309 having a plurality of apertures 310–314. There are five apertures in total, two of which (311, 313) are adjacent to the detection zones and the others (310, 312 and 314) lie in positions on either side of these detection zone apertures. The apertures are of slit form corresponding to the detection lines on the strip. The width of each of the two apertures 311 and 313 corresponding to the detection zones themselves is double the width of each of the three other apertures, which act as controls.

The light passing through these apertures travels down a corresponding slot 315–319 in a baffle plate 320. At the far end of each slot is a light detector 321. The detectors 321 are of identical size and specification. At the front face 322 of the baffle plate 320, each slot is of the same size as the corresponding aperture. At the rear face of the baffle adjacent to the light detectors each slot is of the same size as the face of the light detector adjacent to it. Accordingly, the two slots (316, 318) associated with the detection zone apertures are parallel-sided. The three slots (315, 317 and 319) associated with the control apertures increase in size as they progress towards the light detector.

The slot in the monitor can also accommodate gripping or biasing means such as one or more spring-loaded plates or pins (not shown) to further enhance the positive location of the assay device within the slot.

Ideally, the same optical signal is derived from each aperture irrespective of the precise line position opposite the apertures. The apertures can be of different sizes to promote this objective. The dimensions of the reference zone should be chosen to correspond as closely as possible with the actual area of the detection zone on the strip.

To reduce the possibility of cross-talk between the apertures, the assay strip should be held as close as possible to the apertures when the assay device is located in the slot in the monitor.

As described above, there are five optical measurement channels in the reading device. In addition, there can be a sixth electronic reference channel that provides calibration of the electronic gains in the detector circuitry.

A typical test strip may exhibit a gradient of detectable label concentration along its length, against which the detectable label at a reaction zone must be measured. To accommodate this measurements are ideally made either side of the reaction zone on the test strip. The signal from the reaction zone can be expressed as a ratio of the total signal recorded from the two adjacent reference areas on the strip.

The five measurement channels are divided into two reaction zones and three reference zones. One reference zone, located between the two reaction zones provides a reference optical measurement to both reaction zone measurements.

A reflectance measuring system must all be mounted on one side of the test strip. To achieve the same level of compactness for a five channel reading device would require the use of (relatively) expensive custom components. A transmission design can be made entirely from commercially-available, high volume optoelectronic components, facilitating the production of a monitor that is compact and relatively cheap.

The five detectors 321 are mounted on the back face of a baffle plate. Each detector views the test strip through an aperture in the baffle. The baffle prevents light viewed through one aperture from falling on adjacent detectors, and also provides accommodation for line placement tolerance. The position of the test zone within the field of view of a detector may vary from one edge of the aperture to the other in the x-axis. Any variation in the signal arising from this effect is a function of the angular displacement relative to the centre of the measuring detector. The depth of the baffle can be chosen to control the possible angular displacement of the test zone with respect to the detector, and to maintain the accuracy of the reading.

The projection 305 is maintained in precise location with respect to the apertures. The reference pin locates into depression 207 in the test device casing. This depression is also precisely located with respect to the internal pin 208 moulded into the test device, on which the test strip is located by it's own locating hole punched through the strip. The reaction zones are precisely located with respect to the locating hole. In this manner, within manufacturing tolerances, the reaction zones are held in precise positions with respect to the apertures through which the detectors view the test strip.

The illuminator can consist of a series of LEDs embedded in or placed behind a diffusing medium which provides a uniform and diffuse illumination of the test strip covering the reference and signal zones.

The incorporation of a diffuser between the apertures and the test strip is beneficial for calibration purposes. In order to calibrate each of the optical channels in the absence of the test strip it is highly desirable that each detector is collecting light from the same areas of the illuminator as is the case when a test device is present. The diffuser can be selected to be the dominant diffuser in the optical path so that the introduction of the test strip does not contribute significantly to changes in the illumination distribution observed by the detectors. In addition, the diffuser element can enable the optical assembly to incorporate a 'wipe clean' surface, desirable for long-term repeated performance of the optical assembly. By modulating the intensity of the illuminator, the optical channels can be calibrated, without the aid of moveable parts, 'invisibly' to the user prior to the insertion of a test device.

The test strip can consist of an optically diffuse layer of nitrocellulose or the like, preferably sandwiched between two layers of optically clear film, e.g. of polyester such as "Mylar". The clear film protects the nitrocellulose within which the assay reactions take place. Making reflectance measurements through thin transparent films is particularly difficult because of problems arising from specular reflections. Transmission measurement allows the optics to be constructed orthogonal to the measuring surface and minimises the adverse effects of reflection.

The invention is particularly applicable to the reading of test strips made of nitrocellulose and similar diffuse membranes that preferably do not exceed about 1 mm thickness.

Figure 4A:
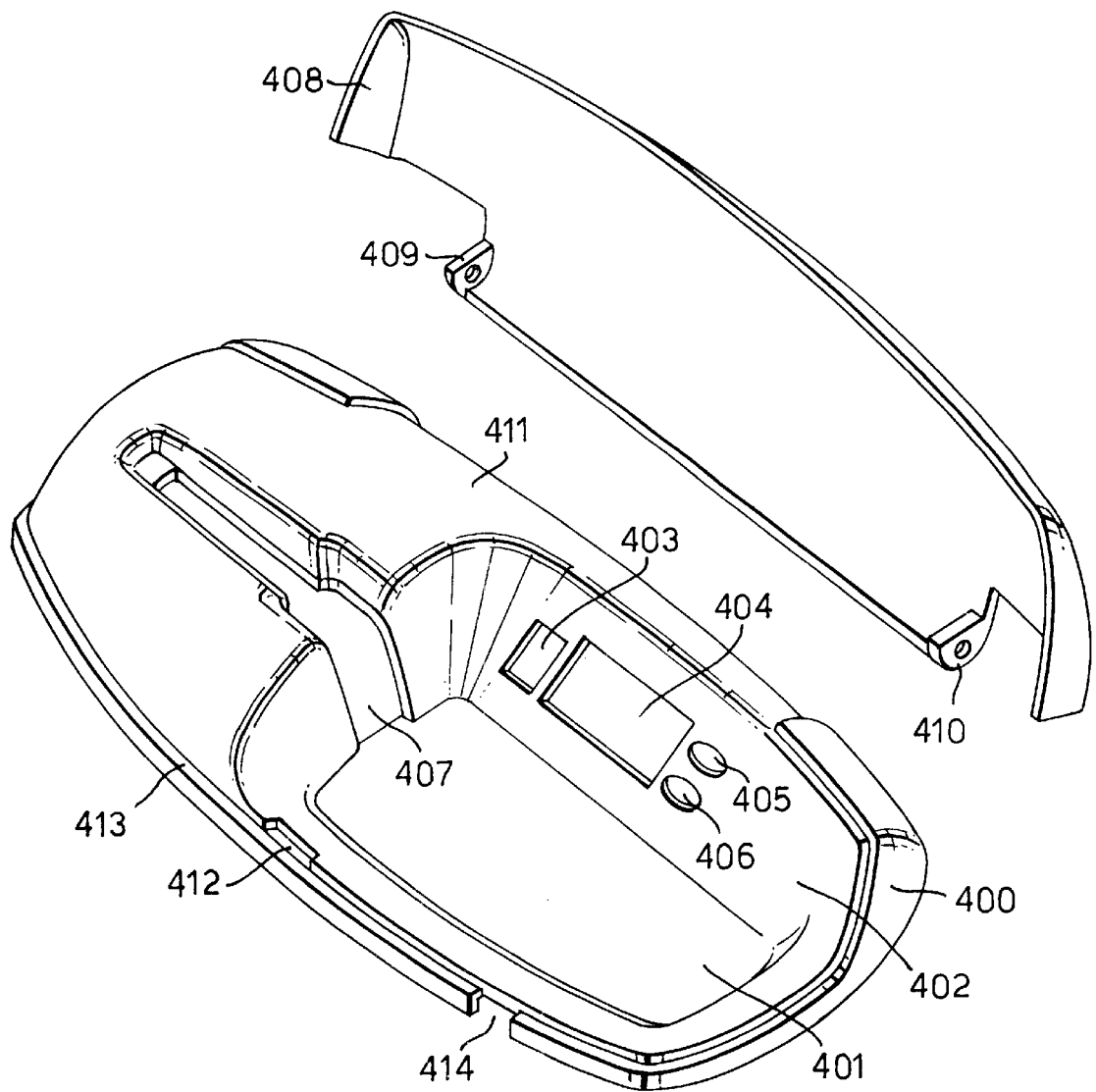

Turning to FIG. 4a, the monitor comprises a moulded casing, eg. of plastics material, having a generally oval rounded shape. The casing principally comprises an upper half 400 and a lower half, only the upper half of which is seen in FIG. 4a. Towards the right hand side of casing 400 is a recess 401 having a backwardly sloping rear face 402. Rear face 402 incorporates an aperture 403 for a push button (not shown), a window 404 to reveal a display panel (not shown) and two windows 405 and 406 to reveal coloured lights or other indicators (again not shown) to convey information to the user. Extending from the left end of recess 401 is a long slot 407 to provide access to a reading head (not shown). Recess 401 and slot 407 are closable by means of a lid 408 which is attached to the rear of the casing by two hinge points 409 and 410. The upper surface 411 of casing 400 is recessed slightly to accommodate the lid when closed, so that the exterior of the closed device presents a relatively smooth continuous surface of the user. The lid can be flipped up to reveal the user-accessible features of the monitor. The lid is closable by means of a spring clip (not seen in FIG. 4a) which extends upwards through an orifice 412 in the front edge 413 of the casing. Front edge 413 of the casing incorporates a further orifice 414 through which a further indicator light (not shown) may be revealed.

Turning to FIG. 4b, the circuit board 430 is of rounded rectangular shape to match the interior shape of the casing, and carries all of the operational features of the monitor. These include a push button 431 which the user can press to initiate the monitoring of an ovulation cycle. When the circuit board is mounted within the casing and covered by upper half thereof, the push button is accessible through aperture 403. To the right of the push button is a visual display panel 432 such as a liquid crystal display which is visible to the user through window 404. To the right of the display panel are two light guides 433 and 434 which transfer, for example, coloured light (such as red and green) from two LEDs or similar lamps (not shown). Appropriate "chips" and memory circuits 435, 436 are mounted on the circuit board. A further light guide 437 mounted at the front edge 438 of the circuit board can convey light from another LED (not shown) to aperture 414. This light may indicate, for example, to the user that an assay is required. This light can be a different colour from the lights associated with display panel, eg. yellow. A battery connector 439 hangs from beneath the circuit board for connection to batteries retained in the lower casing (see FIG. 4c). Also at the front of the circuit board is a switch 440 operable by the spring catch of lid 408.

At the left hand end of the circuit board is mounted the reading head 441 which comprises a central receiving slot 442 to accommodate one end of an assay device (not shown). On the front of receiving slot 442 is an illuminator 443 and immediately opposite at the rear of the slot is an optical sensing system 444 so that light can be passed across the slot (and through a testing device when inserted) and evaluated by the sensor.

Figure 4C:
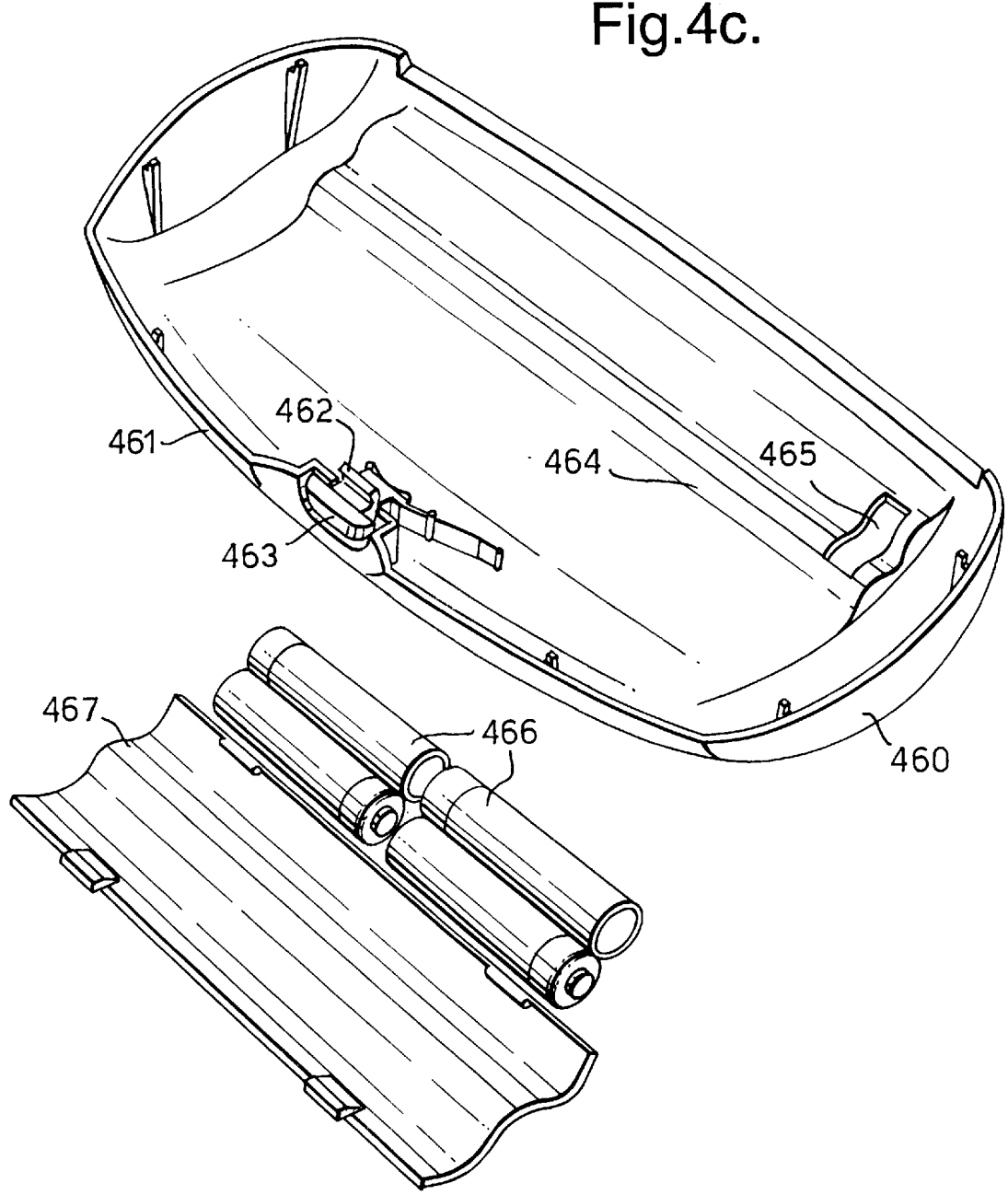

Turning to FIG. 4c, the lower half 460 of the casing has an overall oval shape to match the upper half 400 and provides accommodation for the circuit board 430. The front edge 461 of the casing 460 accommodates a spring loaded catch 462 to fasten lid 408 when closed. Catch 462 is released by pressure on the front face 463 eg. applied by a finger tip. The floor 464 of the casing includes a battery chamber (beneath), and a small access hole 465 is provided towards the right hand end of the casing through which the battery connector 439 can be passed and linked to batteries 466. The batteries are retained by a cover 467 which can be clipped to the underside 468 of the casing.

The constituent parts of the casing can be moulded from high impact or similar plastics materials such as polystyrene and polycarbonate and held together by "push fit" clips of threaded screws or any other appropriate mechanism.

Figure 5:
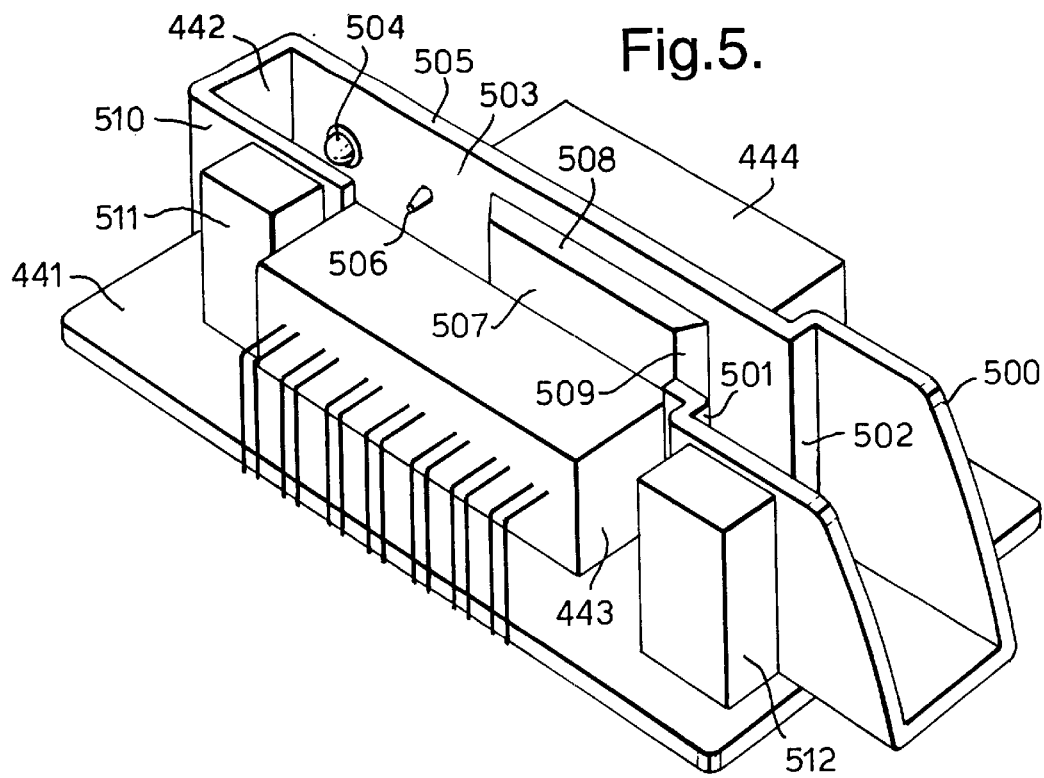
FIG. 5 shows the reading head seen in FIG. 4b on an enlarged scale.

Turning to the enlarged illustration of the reading head, as seen in FIG. 5, the slot 442 for receipt of an assay device is of parallel sided form, but its width is enlarged at its right hand end 500 in a stepped manner to provide a pair of shoulders or abutments 501, 502 against which a correspondingly enlarged portion of an assay device can be abutted. This can facilitate effective insertion of an assay device into the reading head. Within the narrower working part 503 of the slot is a button 504 mounted on the rear wall 505 of the slot, which must be fully depressed to activate the reading mechanism. Appropriate insertion of a testing device causes adequate depression of this button.

Also on the rear wall 505 of the slot is a fixed locating pin 506 which must engage with a corresponding hole in an inserted assay device. Also on the rear wall 505 is a light-transmitting panel 507 which covers the optical sensors. Panel 507 extends outwardly beyond the plane of rear wall 505 of the slot and has sloping edges 508, 509 to give it a distinctive profile. At opposite ends of the front wall 510 of the slot are two pins (not seen in FIG. 5) which are biased outwardly into the slot, e.g. by spring mechanisms contained within two housings 511, 512.

Figure 6:
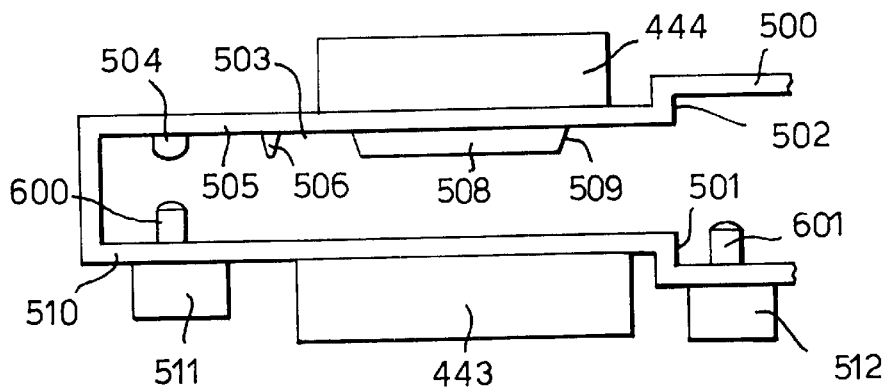
FIG. 6 shows a view directly downwards into the test device receiving slot of the reading head of FIG. 5.

These same features are illustrated in FIG. 6 which is a view directly downwards into the receiving slot. The two biased pins 600, 601 are seen. The purpose of these pins is to provide biasing means to push an inserted assay device against the rear wall 505 of the slot. If the receivable portion of an assay device has appropriately shaped holes or depressions to accommodate the fixed locating pin 506 and the projecting panel 507, the assay device can be pressed sufficiently closely to the rear wall of the slot to depress the button 504 and initiate the optical sensing procedure.

Figure 7:
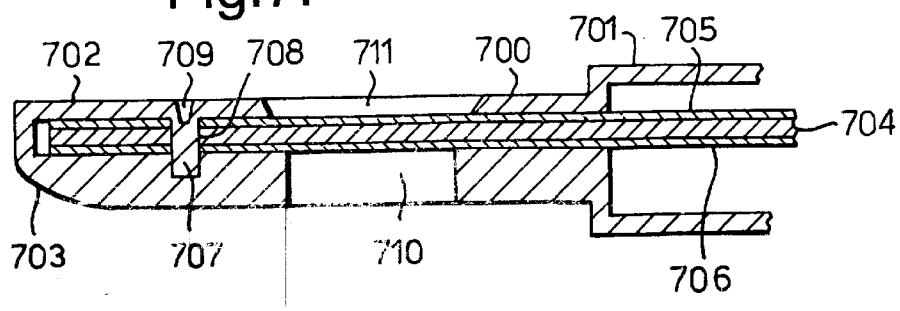
FIG. 7 is a cross-section of one end of a test device designed for insertion into the receiving slot of the reading head.

FIG. 7 shows, in cross-section, part of an assay device 700 having a profile which can cooperate with the features seen in FIG. 6. The assay device can be inserted into the slot with the broader central portion 701 abutting against shoulders 501, 502. The leading end 702 of the assay device has a slightly bevelled edge 703 to facilitate insertion into the slot past pin 600. The assay device comprises a hollow casing containing a porous assay strip 704 sandwiched between two sheets 705, 706 of transparent material. As described earlier, strip 704 is precisely located within the assay device casing by means of a pin 707 which extends through a hole 708 in the strip. On the outside of the assay device casing at a point corresponding to the centre of the locating pin 707 is a conical hole 709 which can accommodate the fixed locating pin 506 in the reader slot. Each side of the assay device casing has an aperture 710, 711 which, when the assay device is inserted in the slot correctly, will be adjacent the light source 443 and light sensors 444 respectively. The profiles of these two apertures are different and in particular the profile of the aperture 711 on the same face of the assay device as the conical hole 709 is shaped to match the profile of the projecting panel 507 covering the light sensors. This ensures that the reading head will only operate when the assay device is inserted in the correct orientation to ensure that the button 504 is depressed.

It will be appreciated that the overall layout and general shape of the monitor can be subject to very considerable variation from that described above without departing from the scope of the invention. The general shape and layout of the reading head is dictated by the need to cooperate effectively with the assay device but this shape can be varied considerably. The layout and nature of the user accessible controls and information display features can likewise be subject to considerable variation and are dictated to a large extent by aesthetic considerations.

The detailed electronics of a monitoring device capable of assimilating, remembering and handling analyte concentration data, as well as providing the preferred electronic features of the device discussed herein, and are appropriate predicting future events, such as the fertility status in an ovulation cycle on the basis of such data, can readily be provided by those skilled in the electronics art once they have been advised of the factors that such a device must take into consideration, and the information that the device must provide for the user. By way of example only, the basic functions that may be required in such a device are outlined in FIG. 8 of the accompanying drawings and described briefly below. The individual features can be entirely conventional, and those familiar with the art of electronics will appreciate that other combinations and arrangements of such features can be employed to achieve the objectives of the invention. For example, so-called "hard-wired" systems, and "neural networks", can be used in place of conventional microprocessors based on "chip" technology.

Figure 8:
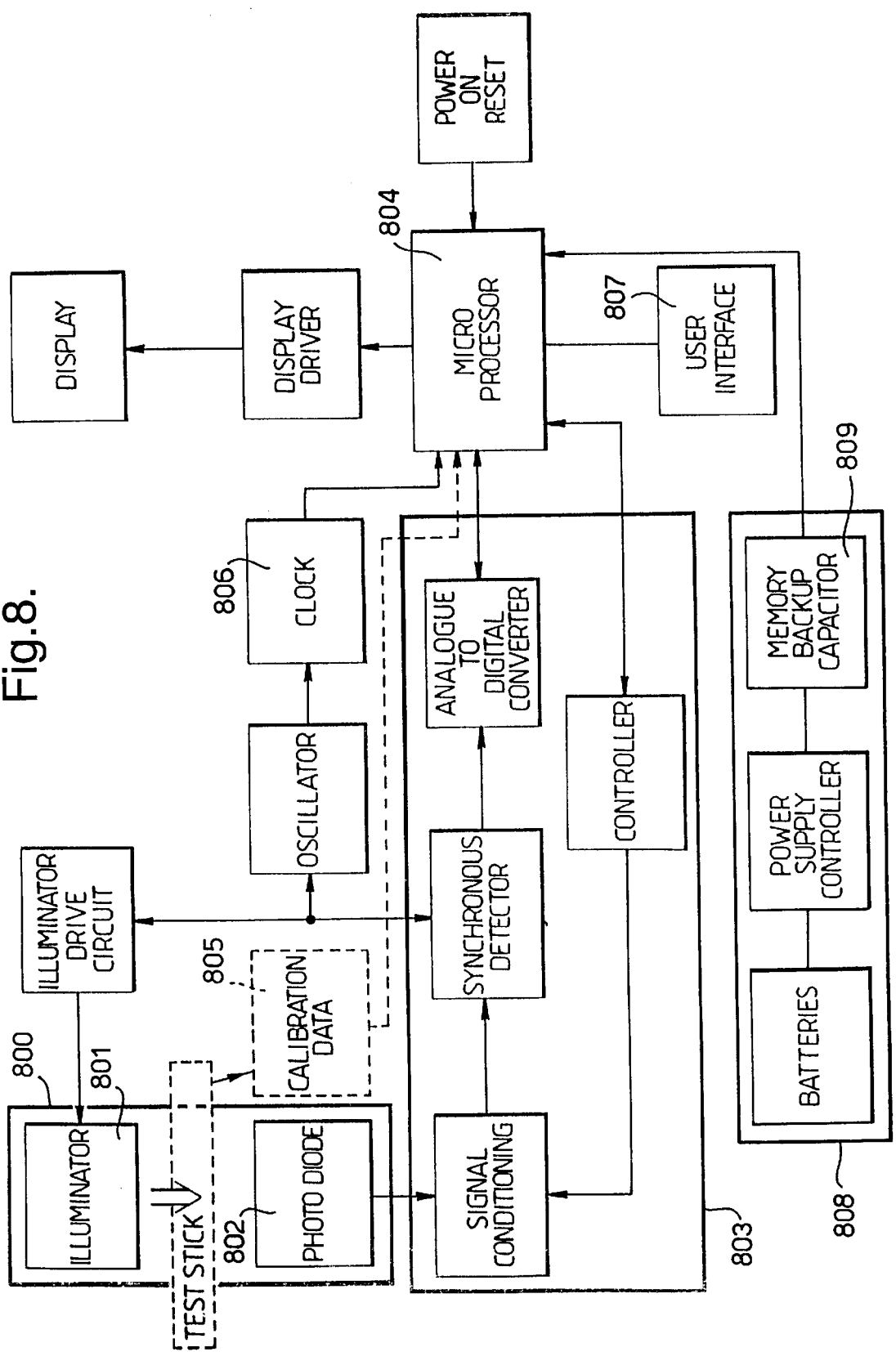
FIG. 8 shows, in schematic form, the basic functions that may be required in an electronic monitor for use in accordance with the invention, as applied to the human ovulation cycle.

As depicted in FIG. 8, the combination essentially comprises a reading unit 800 to derive information from a test device, such as an assay strip, the reading unit comprising an illuminator 801 and a reader 802 (represented here as a photo diode). The reading unit feeds into a conversion unit 803 to convert the optical signal into a form usable by a microprocessor 804. As an optional feature, a calibration system 805 is provided to convert the signal derived from the reading unit into data corresponding, for example, to an absolute concentration value.

A timer, such as a clock 806 may be required to regulate measurements within a cycle. The microprocessor 804 processes, memorizes and interprets results in the light of previous events, particularly recorded from previous cycles. The user interface 807 will generally comprise at least means, such as a push button, which the user can operate at the commencement of a cycle to initiate the operation of the device as a whole. The power supply 808 should include means, such as a memory back-up capacitor 809, to prevent loss of historical data when it becomes necessary to replace batteries.

Information can be conveyed to the user by means of a liquid crystal or LED display, for example. If desired, information on the state of fertility can be conveyed by a simple visual indication, eg a combination of colours showing, for example, green for infertile and red for fertile. Especially if the device is intended primarily as an aid to contraception, it should "fail safe" by showing a "fertile" signal.

As described above, features 803 and 806 together correspond to feature 435 (FIG. 4b), and feature 804 corresponds to feature 436 (FIG. 4b).

Transmission spectrophotometry is a widely used technique for the quantification of dye concentrations in clear liquid solutions. Commercially available spectrophotometers generally require substantial modification to make measurements on diffuse (scattering) solutions. Transmission spectrophotometry is not generally thought of an appropriate method of measuring highly diffuse samples so it is generally only adopted where an alternative approach cannot be applied. For the purposes of the invention, transmission measurement offers positive benefits over the more usual reflectance approach previously employed on test strips.

Some conventional strip assays employ reflectance measurement to assess dye concentration on the strip surface (e.g. glucose monitors). The chemistry of these assays occurs in a very thin layer on the surface of a test strip. In contrast, the chemistry of the preferred strip devices of the invention takes place throughout the thickness of the test strip. Because of variations in flow and reagent deposition, the concentration of detectable label captured at a reaction zone may differ according to depth.

Curvature, surface materials, finish and solvent effects may vary the ratio of specular to diffuse reflection. For reflectance measurements it is the diffusely reflected light from the surface of the strip that carries the signal information (i.e. that light will have interacted with the detectable label), whilst the specularly reflected light will contain no information (as this light is the component that has just bounced off the surface without interacting with the detectable label in the diffuse strip). Without resorting to relatively bulky and expensive systems, it is difficult to design a reflectance measurement system that minimises specular reflection to the extent possible with transmission measurement, especially using diffuse light as in accordance with the invention.

Reflectance systems require the use of a test surface that must be removed from the optical path for the purposes of calibration. This reference surface must not deteriorate if it is to form a part of the optical assembly. In addition, mechanical movement is required to displace such a reference material when an assay strip needs to be measured. Such problems are avoided by the invention.

In addition to the specific examples of detectable materials already mentioned herein, the invention can use as labels materials which block or reflect the electromagnetic radiation, rather than absorb it, e.g. "white" particles such as latex particles in their natural uncoloured state. Alternatively, the label can be a reactant or catalyst which participates in the generation of a radiation absorbing or radiation-blocking material, e.g. an enzyme which reacts with a substrate to produce a detectable material, such as a coloured material, in the detection zone.

EXAMPLES

Aspects of the invention are illustrated in the following Examples. These relate to the monitoring of the human ovulation cycle.

Example 1

This example sets out a convenient algorithm on which a monitoring method in accordance with the invention can be based. The kit provided to the user comprises a plurality of dual-analyte disposable urine testing devices, capable of assaying urinary E3G and urinary LH in a form readable by a monitor also provided. The disposable testing devices and the monitor are as described above. The monitor can receive each used testing device and determine the urinary concentration of each analyte. This information is stored in the monitor and compared with similar data obtained on subsequent days in the same cycle. The monitor has a menstruation button that the user must press at the start of the cycle, and a display panel or the like to convey information about cycle status, and to indicate to the user when testing should be performed.

a) Algorithm rule structure

The objectives are to:
i) identify the position of the LH surge in an individual cycle;
ii) identify a significant increase in E3G concentration in an individual cycle with respect to the E3G concentration on day 6 of that cycle;
iii) preferably, include a fail-safe procedure in the event of failure to identify a significant increase in E3G concentration within an expected interval.

The number of tests available each routine month is limited to 8, and a test strategy which will maximise the chances of achieving i) and ii) is adopted.

b) Start-up cycles

In order to establish an adequate initial data base, during the first cycle of use the monitor requires sixteen tests. This is to establish baseline data for the individual. The user presses the menstruation button on the monitor on the morning after her menstruation begins. This day is recorded as day 1 by the monitor. Testing commences on day 8 and continues daily until day 23. This testing is targeted to maximize the chance of observing the LH surge.

At the start of cycle 2 and the start of all following cycles, the menstruation button is pressed as above. From cycle 2 onwards, eight tests only are used for each cycle. All eight tests must be from the same batch and all must be completed. In all cycles from cycle 2 onwards, testing commences on day 6. For cycles 2 and 3, tests two to eight are conducted on consecutive days starting on the typical LH surge day minus four days. From cycle 4 onwards, regarded as the first routine cycle, tests two to eight are conducted in sequence from typical LH surge minus five days. The typical LH surge day is defined as the mean day of LH surge for up to the previous six months.

c) Start of the fertile phase

In cycle 1, the monitor declares the woman fertile from day 6 onwards, as no information about cycle characteristics has been collected. In cycles 2 and 3, the monitor can use the typical position of the LH surge from the previous cycle(s) to determine the start of the fertile phase. However, because of the limited amount of cycle data available, the monitor will still declare a woman fertile during cycles 2 and 3 on day 6 or on typical LH surge minus 7 days, whichever is later.

In subsequent routine cycles, the onset of the fertile phase is set by detection of a significant change in the E3G signal with respect to day 6. When the ratio of the current day's signal for E3G ($S_t$) to the day 6 signal ($S_6$) reaches a set threshold as set forth above, the woman is declared fertile. As a fail-safe, the monitor declares the woman fertile on the typical LH surge minus 2 days, in the absence of an earlier detected significant change in the E3G signal.

d) End of the fertile phase

In normal operation, the end of the fertile phase is defined as the fourth morning after the detection of the LH surge. In the absence of a detectable LH surge during the test sequence, the system declares the end of the fertile phase to be six days after the last test. The rationale for this calculation is as follows. The testing regime is designed to cover the typical position of the LH surge plus one day. Published WHO study data showed within-woman variability of LH surge position to be 1.8 days. Adding five days to the declared fertile period after testing has been completed allows two standard deviations confidence that the LH surge will occur within the assigned fertile period.

In non-normal operation (cycle 1), where the monitor has no information about the typical LH surge position, if this parameter is not detected, the end of the fertile phase is declared on cycle day 28.

Example 2

This example uses representative E3G profiles from two women—one known to have low levels of urinary E3G and the other known to have relatively high levels. In the first two columns of each table, 30 days of each cycle are set out in terms of their fertility. The first phase is termed infertile and consists of that portion of the follicular phase during which unprotected intercourse would not be expected to result in conception, followed by a transitional phase during which changes occur that lead to a fertile state and during which a positive signal to indicate the onset of the fertile phase is required. The fertile phase is that phase before and after ovulation during which unprotected intercourse is most likely to result in conception. Its duration before ovulation is dictated entirely by the effective lifetime of sperm, and this, in turn is influenced by factors controlled by the female hormones, especially mucus. The post fertile, luteal phase is that time after which the ovum has left the uterus and conception in the current cycle is no longer possible.

E3G values are given in the third column. These were derived by immunoassay on early morning urine samples collected each day. The immunoassay was a conventional enzyme-labelled-antigen competitive assay. The values given are in ng/ml.

Actual ovulation is taken as 24 hours following the LH surge. These LH values were determined by conventional enzyme-labelled sandwich immunoassay on the same samples, but the values are not included in the table as ovulation date is the essential result.

The algorithm of Example 1 has been applied to each cycle, taking the E3G trigger point as:

$$\frac{[i] > 2}{[\text{day } 6]}$$

INDIVIDUAL A

CYCLE A 1: Start-up cycle

| Day | Test | Phase | E3G value | "Red" status | Actual ovulation |
|---|---|---|---|---|---|
| 1 |  | infertile |  |  |  |
| 2 |  | " |  |  |  |
| 3 |  | " |  |  |  |
| 4 |  | " |  |  |  |
| 5 |  | " |  |  |  |
| 6 |  | " |  | *** |  |
| 7 |  | " |  | *** |  |
| 8 | * | " | 1.9 | *** |  |
| 9 | * | " | 3.1 | *** |  |
| 10 | * | " | 5.4 | *** |  |
| 11 | * | " | 2.1 | *** |  |
| 12 | * | " | 5.3 | *** |  |
| 13 | * | " | 10.5 | *** |  |
| 14 | * | " | 7.7 | *** |  |
| 15 | * | fertile | 5.2 | *** |  |
| 16 | * | " | 8.3 | *** |  |
| 17 | * | " | 6.8 | *** |  |
| 18 | * | " | 4.3 | *** | LHS + 1 |
| 19 | * | " | 4.9 | *** |  |
| 20 | * | " | 5.3 | *** |  |
| 21 | * | postfertile | 3.3 |  |  |
| 22 | * | " | 4.9 |  |  |
| 23 | * | " | 6.2 |  |  |
| 24 |  | " | 6.2 |  |  |
| 25 |  | " |  |  |  |
| 26 |  | " |  |  |  |
| 27 |  | " |  |  |  |
| 28 |  | " |  |  |  |
| 29 |  | " |  |  |  |
| 30 |  | " |  |  |  |

LH surge was on day 17, therefore repeated testing to commence on day 13 in next cycle.

Cycle A 2

| Day | Test | Phase | E3G value | "Red" status | Actual ovulation |
|---|---|---|---|---|---|
| 1 |  | infertile |  |  |  |
| 2 |  | " |  |  |  |
| 3 |  | " |  |  |  |
| 4 |  | " |  |  |  |
| 5 |  | " |  |  |  |
| 6 | * | " | 3.5 |  |  |
| 7 |  | " |  |  |  |
| 8 |  | " |  |  |  |
| 9 |  | " |  | *** |  |
| 10 |  | " |  | *** |  |
| 11 |  | " |  | *** |  |
| 12 |  | " |  | *** |  |
| 13 | * | " | 8.9 | *** |  |
| 14 | * | fertile | 14.6 | *** |  |
| 15 | * | " | 12.6 | *** |  |
| 16 | * | " | 8.8 | *** |  |
| 17 | * | " | 15.8 | *** | LHS + 1 |
| 18 | * | " | 6.9 | *** |  |
| 19 | * | " | 6.5 | *** |  |
| 20 |  | postfertile |  |  |  |
| 21 |  | " |  |  |  |
| 22 |  | " |  |  |  |
| 23 |  | " |  |  |  |
| 24 |  | " |  |  |  |
| 25 |  | " |  |  |  |
| 26 |  | " |  |  |  |
| 27 |  | " |  |  |  |
| 28 |  | " |  |  |  |
| 29 |  | " |  |  |  |
| 30 |  | " |  |  |  |

Mean LHS of cycles A1 and A2 is day "16.5", therefore repeated testing to commence on day 12 in next cycle.

Cycle A 3

| Day | Test | Phase | E3G value | "Red" status | Actual ovulation |
|---|---|---|---|---|---|
| 1 |  | infertile |  |  |  |
| 2 |  | " |  |  |  |

-continued

| Day | Test | Phase | E3G value | "Red" status | Actual ovulation |
|---|---|---|---|---|---|
| 3 | | " | | | |
| 4 | | " | | | |
| 5 | | " | | | |
| 6 | * | " | 1.6 | | |
| 7 | | " | | | |
| 8 | | " | | *** | |
| 9 | | " | | *** | |
| 10 | | " | | *** | |
| 11 | | " | | *** | |
| 12 | * | fertile | 6.2 | *** | |
| 13 | * | " | 23.6 | *** | |
| 14 | * | " | 21.3 | *** | |
| 15 | * | " | 9.3 | *** | LHS + 1 |
| 16 | * | " | 4.5 | *** | |
| 17 | * | " | 3.7 | *** | |
| 18 | * | postfertile | 3.4 | | |
| 19 | | " | | | |
| 20 | | " | | | |
| 21 | | " | | | |
| 22 | | " | | | |
| 23 | | " | | | |
| 24 | | " | | | |
| 25 | | " | | | |
| 26 | | " | | | |
| 27 | | " | | | |
| 28 | | " | | | |
| 29 | | " | | | |
| 30 | | " | | | |

Mean LHS from cycles A1 to A3: day "15.7". Repeated testing commencement day for first routine cycle: day 10. Fail-safe day for the first routine cycle: day 13.

Cycle A 4

First routine cycle

| Day | Test | Phase | E3G value | "Red" status | Actual ovulation |
|---|---|---|---|---|---|
| 1 | | infertile | | | |
| 2 | | " | | | |
| 3 | | " | | | |
| 4 | | " | | | |
| 5 | | " | | | |
| 6 | * | " | 3.1 | | |
| 7 | | " | | | |
| 8 | | " | | | |
| 9 | | " | | | |
| 10 | * | " | 6.1 | | |
| 11 | * | fertile | 16.7 | *** | |
| 12 | * | " | 10.8 | *** | |
| 13 | * | " | 22.8 | *** | |
| 14 | * | " | 2.13 | *** | LHS + 1 |
| 15 | * | " | 9.4 | *** | |
| 16 | * | " | 12.2 | *** | |
| 17 | | postfertile | | | |
| 18 | | " | | | |
| 19 | | " | | | |
| 20 | | " | | | |
| 21 | | " | | | |
| 22 | | " | | | |
| 23 | | " | | | |
| 24 | | " | | | |
| 25 | | " | | | |
| 26 | | " | | | |
| 27 | | " | | | |
| 28 | | " | | | |
| 29 | | " | | | |
| 30 | | " | | | |

Days warning of actual ovulation: 3 Mean LHS from cycles A1 to A4: day "15.3". Repeated testing commencement day for next cycle: day 10. Fail-safe day for the next cycle: day 13.

Cycle A 5

Second routine cycle

| Day | Test | Phase | E3G value | "Red" status | Actual ovulation |
|---|---|---|---|---|---|
| 1 | | infertile | | | |
| 2 | | " | | | |
| 3 | | " | | | |
| 4 | | " | | | |
| 5 | | " | | | |
| 6 | * | " | 4.8 | | |
| 7 | | " | | | |
| 8 | | " | | | |
| 9 | | " | | | |
| 10 | * | " | 8.5 | | |
| 11 | * | " | 7.3 | | |
| 12 | * | " | 6.3 | | |
| 13 | * | " | 7.0 | *** | |
| 14 | * | fertile | 11.8 | *** | |
| 15 | * | " | 19.3 | *** | |
| 16 | * | " | 18.5 | *** | |
| 17 | | " | | *** | LHS + 1 |
| 18 | | " | | *** | |
| 19 | | " | | *** | |
| 20 | | postfertile | | | |
| 21 | | " | | | |
| 22 | | " | | | |
| 23 | | " | | | |
| 24 | | " | | | |
| 25 | | " | | | |
| 26 | | " | | | |
| 27 | | " | | | |
| 28 | | " | | | |
| 29 | | " | | | |
| 30 | | " | | | |

Days warning of actual ovulation: 4 (triggered by fail-safe) Mean LHS from cycles A1 to A5: day "15.4". Repeated testing commencement day for next cycle: day 10. Fail-safe day for the next cycle: day 13.

INDIVIDUAL B

CYCLE B1: Start-up cycle

| Day | Test | Phase | E3G value | "Red" status | Actual ovulation |
|---|---|---|---|---|---|
| 1 | | infertile | | | |
| 2 | | " | | | |
| 3 | | " | | | |
| 4 | | " | | | |
| 5 | | " | | *** | |
| 6 | | " | | *** | |
| 7 | | " | | *** | |
| 8 | * | " | 25.1 | *** | |
| 9 | * | " | 10.1 | *** | |
| 10 | * | " | 16.8 | *** | |
| 11 | * | " | 28.2 | *** | |
| 12 | * | " | 24.6 | *** | |
| 13 | * | " | 28.7 | *** | |
| 14 | * | " | 27.7 | *** | |
| 15 | * | " | 62.6 | *** | |
| 16 | * | " | 68.5 | *** | |
| 17 | * | fertile | 61.9 | *** | |
| 18 | * | " | 103.4 | *** | |
| 19 | * | " | 85.4 | *** | |
| 20 | * | " | 45.4 | *** | LHS + 1 |

CYCLE B1: Start-up cycle (continued)

| Day | Test | Phase | E3G value | "Red" status | Actual ovulation |
|---|---|---|---|---|---|
| 21 | * | " | 14.9 | *** | |
| 22 | * | " | 46.6 | *** | |
| 23 | * | postfertile | 49.3 | | |
| 24 | | " | | | |
| 25 | | " | | | |
| 26 | | " | | | |
| 27 | | " | | | |
| 28 | | " | | | |
| 29 | | " | | | |
| 30 | | " | | | |

LH surge was on day 19, therefore repeated testing to commence on day 15 in next cycle.

Cycle B 2

| Day | Test | Phase | E3G value | "Red" status | Actual ovulation |
|---|---|---|---|---|---|
| 1 | | infertile | | | |
| 2 | | " | | | |
| 3 | | " | | | |
| 4 | | " | | | |
| 5 | | " | | | |
| 6 | * | " | 28.9 | | |
| 7 | | " | | | |
| 8 | | " | | | |
| 9 | | " | | | |
| 10 | | " | | | |
| 11 | | " | | | |
| 12 | | " | | *** | |
| 13 | | " | | *** | |
| 14 | | " | | *** | |
| 15 | * | fertile | 62.0 | *** | |
| 16 | * | " | 94.6 | *** | |
| 17 | * | " | 58.4 | *** | LHS + 1 |
| 18 | * | " | 42.4 | *** | |
| 19 | * | " | 60.4 | *** | |
| 20 | * | " | 56.0 | *** | |
| 21 | * | postfertile | 35.0 | | |
| 22 | | " | | | |
| 23 | | " | | | |
| 24 | | " | | | |
| 25 | | " | | | |
| 26 | | " | | | |
| 27 | | " | | | |
| 28 | | " | | | |
| 29 | | " | | | |
| 30 | | " | | | |

Mean LHS from cycles B1 and B2 is day "17.5", therefore repeated testing to commence on day 13 in next cycle.

Cycle B 3

| Day | Test | Phase | E3G value | "Red" status | Actual ovulation |
|---|---|---|---|---|---|
| 1 | | infertile | | | |
| 2 | | " | | | |
| 3 | | " | | | |
| 4 | | " | | | |
| 5 | | " | | | |
| 6 | * | " | 17.2 | | |
| 7 | | " | | | |
| 8 | | " | | | |
| 9 | | " | | | |
| 10 | | " | | *** | |
| 11 | | " | | *** | |
| 12 | | " | | *** | |
| 13 | * | " | 23.9 | *** | |
| 14 | * | fertile | 63.8 | *** | |
| 15 | * | " | 22.1 | *** | |
| 16 | * | " | 65.9 | *** | |
| 17 | * | " | 41.2 | *** | LHS + 1 |
| 18 | * | " | 7.6 | *** | |
| 19 | * | " | 35.3 | *** | |
| 20 | | postfertile | | | |
| 21 | | " | | | |
| 22 | | " | | | |
| 23 | | " | | | |
| 24 | | " | | | |
| 25 | | " | | | |
| 26 | | " | | | |
| 27 | | " | | | |
| 28 | | " | | | |
| 29 | | " | | | |
| 30 | | " | | | |

Mean LHS from cycles B1 to B3: day 17. Repeated testing commencement day for first routine cycle: day 12. Fail-safe day for the first routine cycle: day 15

Cycle B 4

First routine cycle

| Day | Test | Phase | E3G value | "Red" status | Actual ovulation |
|---|---|---|---|---|---|
| 1 | | infertile | | | |
| 2 | | " | | | |
| 3 | | " | | | |
| 4 | | " | | | |
| 5 | | " | | | |
| 6 | * | " | 12.9 | | |
| 7 | | " | | | |
| 8 | | " | | | |
| 9 | | " | | | |
| 10 | | " | | | |
| 11 | | " | | | |
| 12 | * | " | 38.3 | *** | |
| 13 | * | fertile | 70.6 | *** | |
| 14 | * | " | 74.6 | *** | |
| 15 | * | " | 70.6 | *** | |
| 16 | * | " | 49.7 | *** | LHS + 1 |
| 17 | * | " | 23.5 | *** | |
| 18 | * | " | 29.8 | *** | |
| 19 | | postfertile | | | |
| 20 | | " | | | |
| 21 | | " | | | |
| 22 | | " | | | |
| 23 | | " | | | |
| 24 | | " | | | |
| 25 | | " | | | |
| 26 | | " | | | |
| 27 | | " | | | |
| 28 | | " | | | |
| 29 | | " | | | |
| 30 | | " | | | |

Days warning of actual ovulation: 4 Mean LHS from cycles B1 to B4: day "16.5". Repeated testing commencement day for next cycle: day 11. Fail-safe day for the next cycle: day 14

Cycle B 5

| Day | Test | Phase | E3G value | "Red" status | Actual ovulation |
|---|---|---|---|---|---|
| | | Second routine cycle | | | |
| 1 | | infertile | | | |
| 2 | | " | | | |
| 3 | | " | | | |
| 4 | | " | | | |
| 5 | | " | | | |
| 6 | * | " | 7.2 | | |
| 7 | | " | | | |
| 8 | | " | | | |
| 9 | | " | | | |
| 10 | | " | | | |
| 11 | * | " | 14.1 | | |
| 12 | * | " | 17.4 | | |
| 13 | * | " | 41.3 | *** | |
| 14 | * | " | 57.5 | *** | |
| 15 | * | fertile | 42.0 | *** | |
| 16 | * | " | 55.4 | *** | |
| 17 | * | " | 60.1 | *** | |
| 18 | | " | | *** | LHS + 1 |
| 19 | | " | | *** | |
| 20 | | " | | *** | |
| 21 | | postfertile | | | |
| 22 | | " | | | |
| 23 | | " | | | |
| 24 | | " | | | |
| 25 | | " | | | |
| 26 | | " | | | |
| 27 | | " | | | |
| 28 | | " | | | |
| 29 | | " | | | |
| 30 | | " | | | |

Days warning of actual ovulation: 5 LHS detected on last day at testing. Mean LHS from cycles B1 to B5: day "16.6". Repeated testing commencement day for next cycle: day 11. Fail-safe day for the next cycle: day 14

Example 3

This example illustrates a very simple but convenient human contraceptive system, relying solely per cycle on a limited number of assays for the urinary analyte E3G.

The user is provided with a 'monthly' batch of 8 identical disposable assay devices, each comprising an assay strip to which a urine sample can be applied, the strip including all necessary reagents to enable a signal indicative of the E3G concentration to be provided, for example by a competition reaction involving a labelled specific binding reagent which becomes bound in a detection zone on the strip in an amount directly or inversely proportional to the E3G concentration in the urine sample. An optical electronic reader is also provided, which converts signal information from the used strip into numerical data and processes this data to provide the user with appropriate information concerning cycle status.

An initial urine assay is performed on day 6 of the current cycle (day 1 being the day on which menses is first observed), to establish a base reference for the E3G concentration in this cycle.

A second urine assay is performed on day 9, and each day thereafter, until either all tests are used up, or until an indication of an elevated E3G concentration indicative of imminent ovulation is given. A sufficiently elevated E3G concentration is declared when the ratio of the reference concentration [r] to the test concentration [i] first meets the criterion:

$$\frac{[i]}{[r]} \geq 2$$

in the case of direct proportionality between the test signal and the E3G concentration, or $$\frac{[r]}{[i]} \geq 2$$

in the case of inverse proportionality.

Unprotected intercourse is avoided on the day the sufficiently elevated E3G concentration is detected, and for 12 immediately successive days thereafter.

If a sufficiently elevated E3G concentration is not detected before all of the tests have been used, unprotected intercourse is avoided for 15 immediately successive days following the last test day.

As a further fail-safe, the E3G peak (as hereinbefore defined) is used to record the day of ovulation in previous cycles, and the user is advised that the fertile phase has commenced if a sufficiently elevated E3G concentration is not detected prior to 3 days before the mean ovulation day. Conception does not occur.

This example provides the benefit to the user that only a few tests are required per month. Manufacturing simplicity is also provided, because only one analyte (E3G) is assayed.

If desired, the assay can be made more sophisticated, for example by enabling the event of ovulation to be detected by including urinary LH concentration data, and by pooling data from previous cycles, so that the abstinence period may be reduced further without increasing the likelihood of conception, as described generally hereinbefore.

Example 5

This Example illustrates a combined LH/E3G assay according to the invention. The physical construction and methods of manufacture of appropriate devices, including manufacture of reagents, are described in detail in EP-A-291194 and EP-A-383619.

The E3G latex is prepared by combining blue-coloured latex particles (mean diameter 380 nm) with an anti-E3G monoclonal antibody of affinity in solution of about $10^{10}$ liters/mole. The antibody (170 µg/ml) is mixed with latex particles (0.5% solids) in a sodium borate buffer at pH 8.5. Vacant binding sites on the latex surface are blocked with BSA [25 mg/ml]. The latex is then washed to remove non-absorbed materials.

The LH latex is prepared from an anti-beta LH monoclonal antibody adsorbed onto blue-coloured latex particles (380 nm). This process is carried out with an antibody to latex ratio of 100 µg/ml to 0.5% solids in a sodium borate buffer (pH 8.5) containing ethanol (ratio of 6 to 1 v/v), followed by blocking the vacant binding sites with BSA (25 mg/ml). The latex is then washed to remove non-adsorbed materials.

A sheet (1.4 mm thick) of commercially-available, detergent pre-treated, macroporous polyethylene having a pore size of about 100 microns is saturated with an aqueous suspension of equal amounts of both populations of the latex particles as prepared above, 0.008% total solids, in a Tris buffer at pH 8.5 containing 3% BSA and 1% sugar. The sheet is freeze-dried and cut into portions each 6×12 mm, having a liquid capacity of about 50 µL.

The solid phase strip on which the levels of E3G and LH are detected in nitrocellulose, of 8µ nominal pore size, bonded to a polyester backing sheet. An E3G-protein (ovalbumen) conjugate, and an anti-alpha LH antibody, are separately plotted as lines onto the nitrocellulose at different locations (see FIG. 9) using solutions containing 2 mg/ml of the respective reagent in phosphate buffer at pH 7.4. The nitrocellulose is blocked with PVA before being cut into strips.

The above reagents are used in the assembly of an assay device as generally described and illustrated under embodiment 1 of EP-A-383619.

FIGS. 9a and 9b of the accompanying drawings illustrate the device.

FIG. 9a shows the strip 901 of nitrocellulose on a backing strip 902 of transparent polyester. The strip has a length of 40 mm and width 6 mm. Line 903 represents the position of the anti-LH antibody immobilised on the strip. This line is approximately 1 mm wide and is centred 10 mm from the left hand end 904 of strip 1. Line 905 represents the position of the immobilised E3G. This is also a line of about 1 mm width and is centred 16 mm from the left hand end of the strip.

FIG. 9b shows the assembled device in cross-section. The device comprises a casing having an upper half 910 and a lower half 911. A bibulous sample receiving member (wick) 912 protrudes from the left hand end 913 of the casing. The macro-porous body 914 containing the two populations of latex particles is in contact with the wick within the casing. The casing also contains the strip 901 and its associated backing sheet 902. Sample liquid applied to the sample collector 912 can migrate via macro-porous body 914 into strip 901. The casing has an upper aperture or window 914 and a lower aperture or window 916 arranged opposite one another such that light can be passed through the casing from one side to the other and in so doing will pass through a portion of the strip. This portion contains both reagent lines 903 and 905. Terminal portion 917 of the casing can contain a sink or desicant, if desired.

When a urine sample containing LH and E3G is applied to the device it migrates via body 914 and into the strip. The two populations of latex particles are released and conveyed with the sample. Depending on the concentrations of the two analytes in the sample, the latex particles carrying the appropriate binding material become attached to the strip in the lines 903 and 905. The degree of binding of the particles in these lines can be determined by light transmission through the strip, as described in detail above.

The relative positioning of the E3G and LH lines, as described above, considerably enhances the efficiency with which the respective concentrations of the two analytes can be determined.

What is claimed is:

1. A test kit for use in monitoring an ovulation cycle of a female mammal, which kit consists essentially of a plurality of disposable testing devices for sampling and testing a body fluid, and providing readable signals indicative of the concentrations of at least two different analytes in said body fluid, together with an electronic reader/monitor for reading and interpreting said readable signals to provide the user with an indication of the fertility status of said cycle, wherein:
   a) said readable signals are read while one of said testing devices is located within a receiving means of said reader/monitor;
   b) said readable signals are created by concentrating a first detectable material in a first detection zone of a porous carrier within said testing device and by concentrating a second detectable material in a second detection zone of said porous carrier, while said sampled body fluid is flowing through said porous carrier, wherein said flowing body fluid contacts said first detection zone and said second detection zone sequentially;
   c) said first detection zone signal being the result of a sandwich-format specific binding reaction and thereby being directly indicative of the body fluid concentration of a first analyte which first analyte exhibits a detectable concentration change closely associated with the time of actual ovulation;
   d) said second detection zone signal being the result of a competition-format specific binding reaction and thereby is indicative of the body fluid concentration of a second analyte, which second analyte exhibits a detectable concentration change after menses but in advance of the time of actual ovulation;
   e) said second detection zone being downstream from said first detection zone relative to a receiving portion of said testing device which is contacted with said body fluid to initiate said tests, said first detection zone containing an immobilized anti-LH antibody and said second detection zone containing immobilized hapten or an analog thereof;
   f) said readable signals are read by optical transmission through said testing device using pulsed diffuse light; and
   g) the reader/monitor comprising:
      (1) a source of pulsed diffuse light having a wavelength that is strongly absorbed by said detectable materials;
      (2) a sensing means for sensing incident light from said source;
      (3) a receiving means for receiving and holding said testing device with each of said detection zones in a light path between said source and said sensor; and
      (4) an electronic means for deriving detectable material concentration, said electronic means being connected to said sensing means, said electronic means being programmed to derive from sensed incident light a measure of the extend to which detectable material has become concentrated in each of said detection zones.

2. A test kit according to claim 1 for use in monitoring the human ovulation cycle.

3. A test kit according to claim 2 wherein the body fluid is urine.

4. A test kit according to claim 1, wherein said diffuse light is pulsed, and said electronic means is programmed to control said sensing means such that said sensing means only senses incident light in phase with said pulsed light, said light preferably having a pulse frequency of at least about 1 kHz.

5. A test kit as claimed in claim 1, wherein said receiving means incorporates interlocking means engagable with corresponding interlocking means on said testing device to ensure that upon receipt of said testing device by said reader/monitor said detection zones are located and maintained in a predetermined spacial relationship relative to said sensing means.

6. A test kit as claimed in claim 5, wherein said receiving means includes actuating means triggered by said receipt of said testing device, said actuating means causing said reading of said detection zones to be initiated.

7. A test kit as claimed in claim 5, wherein said testing device has a casing or cover which includes internal registration means which engages with corresponding registration means associated with porous said carrier such that said detection zones within said testing device casing or cover are located in a predetermined spacial relationship relative to said interlocking means on said testing device casing or cover.

8. A test kit according to claim 6, wherein said internal registration means comprises a pin, engagable with a hole or indentation in said porous carrier, said detection zones being at predetermined locations on said porous carrier relative to said hole or indentation.

9. A test kit according to claim 1, wherein said readable signals are created by concentrating particle-labelled reagents in the respective detection zones.

10. A test kit according to claim 1, containing a sufficient plurality of disposable testing devices to enable a user to conduct testing on a one-per-day basis for a maximum of 16 days in any one ovulation cycle.

11. A replacement pack containing from about 7 about 12 disposable testing devices to replenish a test kit according to claim 1, plus instructions to the user to use all of said testing devices during the course of one ovulation cycle.

* * * * *